United States Patent
Tang et al.

(10) Patent No.: US 9,493,419 B2
(45) Date of Patent: Nov. 15, 2016

(54) QUINOLINE DERIVATIVES AS ANTI-CANCER AGENTS

(75) Inventors: Johnny Cheuk-on Tang, Hong Kong (CN); Albert Sun Chi Chan, Hong Kong (CN); Kim Hung Lam, Hong Kong (CN); Sau Hing Chan, Hong Kong (CN)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 0 days.

(21) Appl. No.: 13/334,073

(22) Filed: Dec. 22, 2011

(65) Prior Publication Data

US 2012/0165370 A1  Jun. 28, 2012

Related U.S. Application Data

(63) Continuation-in-part of application No. 11/892,188, filed on Aug. 21, 2007, now Pat. No. 9,321,730, and a continuation-in-part of application No. PCT/CN2008/072092, filed on Aug. 21, 2008, which is a continuation of application No. 11/892,188, filed on Aug. 21, 2007, now Pat. No. 9,321,730.

(60) Provisional application No. 61/425,767, filed on Dec. 22, 2010.

(51) Int. Cl.
| | | |
|---|---|---|
| C07D 215/20 | (2006.01) |
| C07D 215/14 | (2006.01) |
| C07D 215/22 | (2006.01) |
| C07D 215/227 | (2006.01) |

(52) U.S. Cl.
CPC ........... *C07D 215/20* (2013.01); *C07D 215/14* (2013.01); *C07D 215/22* (2013.01); *C07D 215/227* (2013.01)

(58) Field of Classification Search
None
See application file for complete search history.

(56) References Cited

U.S. PATENT DOCUMENTS

| | | | |
|---|---|---|---|
| 2,411,670 A * | 11/1946 | Senn .............................. | 546/179 |
| 2,596,978 A * | 5/1952 | Burtner et al. ............... | 430/436 |
| 3,818,012 A * | 6/1974 | Nikles .......................... | 546/175 |
| 5,405,843 A | 4/1995 | Fukazawa et al. | |
| 5,541,196 A | 7/1996 | Fournet et al. | |
| 2009/0054482 A1* | 2/2009 | Chan et al. ................... | 514/311 |

FOREIGN PATENT DOCUMENTS

| | | |
|---|---|---|
| CN | 1219131 A | 6/1999 |
| CN | 1219131 A | 9/1999 |
| CN | 200880110440.5 | 11/2012 |
| JP | 5-09674 A | 4/1993 |
| JP | 10-176053 | 6/1998 |
| JP | 5232233 | 3/2013 |

| | | |
|---|---|---|
| WO | WO 97/44036 | 5/1997 |
| WO | WO 2006/003405 A1 | 1/2006 |
| WO | WO 2007/147217 | 12/2007 |

(Continued)

OTHER PUBLICATIONS

Buchi et al., Synthesis and Pharmacological Activity of Thiosemicarbazones of 8-Hydroxyquinoline Derivatives, 39 Helvetica Chemica Acta 1676-83 (1956).*

(Continued)

*Primary Examiner* — Timothy R Rozof
(74) *Attorney, Agent, or Firm* — Duane Morris LLP; Siegfried J. W. Ruppert

(57) ABSTRACT

Quinoline derivatives showing anticancer activities against cancer cell lines of hepatocellular carcinoma (Hep3B), lung carcinoma (A549), esophageal squamous cell carcinoma (HKESC-1, HKESC-4 and KYSE150). The quinoline derivatives have a backbone structure of the following formulas:

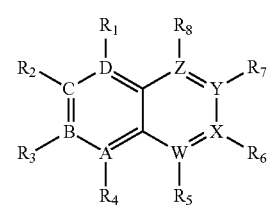

I

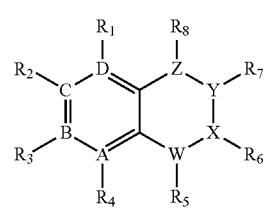

II

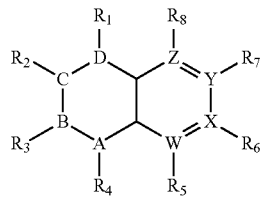

III

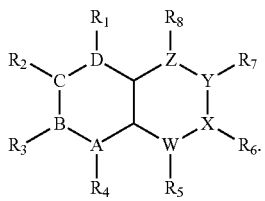

IV

22 Claims, 2 Drawing Sheets

(56) References Cited

FOREIGN PATENT DOCUMENTS

| WO | WO 2007/147217 A1 | 12/2007 |
|----|----|----|
| WO | WO 2008/013966 | 1/2008 |
| WO | WO 2008/013966 A2 | 1/2008 |
| WO | WO 2009/024095 | 2/2009 |
| WO | WO 2009/024095 A1 | 2/2009 |

OTHER PUBLICATIONS

Lam et al., Preparation of Galipea Officinalis Hancock Type Tetrahydroquinoline Alkaloid Analogues as Anti-Tumour Agents, 20 Phytomedicine 166-71 (2013).*

Zhandarev et al., Synthesis & Antibacterial Activity of Tetrahydroquinolin-8-ols, 42(7) Russian J. Org. Chem. 1093-1094 (2006) (CAS Abstract).*

Hodgkinson & Limpach, 63 J.O.C., Transactions 104-110 (1893) (CAS Abstract).*

Hassani et al., 48(24) J. Med. Chem. 7733-7749 (2005) (CAS Abstract).*

Okamoto, K., 61(Suppl. 3) Tohoku J. Exp. Med. 116 (1955) (CAS Abstract).*

Troger & Pape, 114 J. Fuer Praktische Chemie (Leipzig) 199-220 (1926) (CAS Abstract).*

Bourquin et al., 295 Archiv Der Pharmazie Und Berichte Der Deutschen Pharmazeutischen Gesellschaft 383-99 (1962) (CAS Abstract).*

Nagarajan et al., 7(9) Indian J. Chem. 848-58 (1969) (CAS Abstract).*

Nagarajan et al., 12(3) Indian J. Chem. 252-7 (1974) (CAS Abstract).*

Kawase et al., 29(6) Chem. & Pharm. Bull. 1615-23 (1981) (CAS Abstract).*

Kharizanova et al. 11 Trudove Na Nauchnoizsledovatelskiya Khimikofarmatsevtichen Institut 287-93 (1981) (CAS Abstract).*

Ono et al., 5 Chem. Letts. 437-438 (1998) (CAS Abstract).*

Shi et al., 46(29) Angewandte Chemie, Intern'l Ed. 5554-5558, S5554/1-S5554/52 (2007) (CAS Abstract).*

Abramov I. G, et al.; "Synthesis of substituted azines with the participation of 4-bromo-5-nitrophthalonitrile"; Mendeleev Commun., vol. 12, No. 3; Feb. 3, 2006 pp. 120-121.

Maffeo D., et al ; "Intramolecular sensitisation of europium(III) luminescence by 8•benzyloxyquinoline in aqueous solution"; Inorganica Chimica Acta, 355; Dec. 31, 2003; pp. 127-136.

Musiol R,, et al.; "Antifungal properties of new series of quinoline derivatives"; Bioorg. Med. Chem.,14; Feb. 3, 2006; pp. 3592-3598; Abstrct.

Wang W. B., et at.; "Highly Enantioselective Iridium-Catalyzed Hydrogenation of Heteroaromatic Compounds, Quinolines"; J. Am. Chem. Soc. vol. 125, No. 35; Aug. 9, 2008; pp. 10536-10537. Abstract.

Decision to Grant European Patent, Application No. 08784083.1, "The Hong Kong Polytechnic University," dated Oct. 10, 2013, 2 pages.

Communication Under Rule 71(3) EPC, Application No. 08784083.1, "The Hong Kong Polytechnic University," dated Jun. 12, 2013, 45 pages.

Supplemental European Search Report, Application No. 08784083.1, "The Hong Kong Polytechnic University," dated Jul. 18, 2011.

Wang, W., "Highly Enantioselective Iridium-Catalyzed Hydrogenation of Heteroaromatic Compounds, Quinolines," J. Am. Chem. Soc., vol. 125, No. 35 (2003) pp. 6-30.

Musiol, R., et al., "Antifungal Properties of New Series of Quinoline Derivatives," Bioorg. Med. Chem. 14, (2006) pp. 3592-3598.

Maffeo, D., et al., "Intramolecular Sensitisation of Europium(III) Luminescence by 8-benzyloxyquinoline in Aqueous Solution," J.A. G. Williams Inorganica Chimica Acta 355, (2003) pp. 127-136.

Abramov, I., et al., "Synthesis of Substituted Azines with the Participation of 4-bromo-5-nitrophthalonitrile," Mendeleev Commun., (2002) 12(3), pp. 120-121.

Patent Abstracts of Japan corresponds to JP Publication No. 10-176053 dated Jun. 30, 1998.

Statement of Accurate Translation for Chinese Patent No. 200880110440.5, issued Nov. 7, 2012—2 pages.

Statement of Accurate Translation for Japanese Patent No. 5232233, issued Mar. 29, 2013—3 pages.

International Search Report—PCT/CN2008/072092, dated Dec. 11, 2008—4 pages.

Patent Abstract of Japan—Publication No. 05097674A—dated Apr. 20, 1993—1 page.

International Preliminary Report on Patentability—International Appln. No. PCT/CN2008/072092, dated Aug. 21, 2008—9 pages.

"Alkyl." https://en.wikipedia.org/wiki/Alkyl; Last visited: Feb. 12, 2016.

Chan, S.H. et al., "The preparation and in vitro antiproliferative activity of phthalimide based ketones on MDAMB-231 and SKHep-1 human carcinoma cell lines," Eur. J. Med. Chem.(2009) vol. 44(6), pp. 2736-2740.

Casu, F. et al., "Synthesis of 2'-substituted inosine analogs via unusual masking of the 6-hydroxyl group." Nucleosides Nucleotides Nucleic Acids, (2012) vol. 31(3), pp. 224-235.

Kok, S.H., et al., "Synthesis and anti-cancer activity of benzothiazole containing phthalimide on human carcinoma cell lines." Bioorg. Med. Chem. (2008), vol. 16(7), pp. 3626-3631.

Reusch, W. "Hydroxyl Group Substitutions." http://chemwiki.ucdavis.edu/Organic_Chemistry/Alcohols/Reactivity_of_Alcohols/Hydroxyl_Group_Substitution; Last visited:Feb. 12, 2016.

Reusch, W. "Substitution of the hydroxyl group." http://chemwiki.ucdavis.edu/Organic _Chemistry/Carboxylic_Acids/Reactivity_of_Carboxylic_Acids/Reactions_of_Carboxylic_Acids/Substitution_of_the_hydroxyl_group; Last visited: Feb. 12, 2016.

Sambasiva, R.P. et al., "Synthesis of novel 2-alkyl triazole-3-alkyl substituted quinoline derivatives and their cytotoxic activity." Bioorg. Med. Chem. Lett. (2013), vol. 23(5), pp. 1225-1227.

* cited by examiner

QUINOLINE DERIVATIVES AS ANTI-CANCER AGENTS

CROSS REFERENCE TO RELATED APPLICATIONS

This application is a continuation-in-part application of U.S. patent application Ser. No. 11/892,188, filed Aug. 21, 2007, and entitled "METHOD OF MAKING AND ADMINISTERING QUINOLINE DERIVATIVES AS ANTI-CANCER AGENTS, and claims the benefit of (i) PCT/CN2008/072092, filed Aug. 21, 2008, which claims benefit of U.S. patent application Ser. No. 11/892,188, filed Aug. 21, 2007, (ii) Chinese Pat. Appl. No 200880110440.5, filed Aug. 21, 2008, now Chinese Pat. No. 101868447; (iii) Japanese Pat. Appl. No. 2010-521286, filed Aug. 21, 2008, now Japanese Pat. No. 5232233, (iv) European Pat. Appl. No. 08784083.1, filed Aug. 21, 2008, now European Pat. No. 2188259, and (v) U.S. Provisional Pat. Appl. Ser. No. 61/425,767, filed Dec. 22, 2010, the contents of which are incorporated herein in their entireties by reference.

FIELD OF THE INVENTION

This invention relates to a novel genus of compounds useful as anti-cancer agents. Particularly, it relates to a group of substituted quinoline derivatives which show potent anti-cancer effects.

BACKGROUND OF THE INVENTION

Substituted quinoline-type alkaloids are known for possessing interesting biological activities. For example, 8-hydroxyquinoline derivatives were reported to possess activities against (i) Alzheimer's disease, (ii) rat mesenchymal stem cells (rMSCs) proliferation and (iii) antifungal properties. The compound, 8-aminoquinoline (sitamaquine), has been suggested to be a candidate agent for treating visceral *leishmania* leishmaniasis. The 8-hydroxyquinoline and its derivatives have been reported to possess good antifungal properties and can help the treatment of neurodegenerative disease.

Asymmetric hydrogenation offers a new method for structural modification of this compound type to produce new chiral structural moiety and associated bioactivity. Zhou, Chan and others reported their effort in the asymmetric production of chiral tetrahydroquinoline with high enantioselectivities. However, there is no known report of the substituted quinoline-type alkaloids of the present invention that are useful for cancer treatment with good solubility and acceptable cell toxicity.

SUMMARY OF THE INVENTION

The present invention provides quinoline derivatives of formula I-IV and their salts for anti-tumor activities.

Formula I-IV

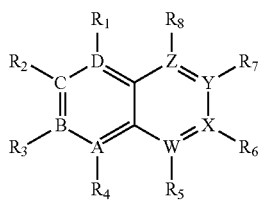

I

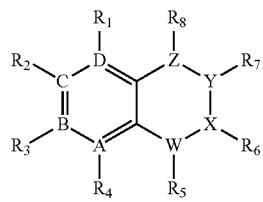

II

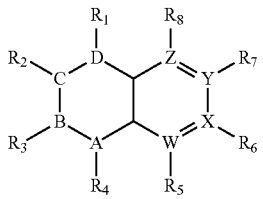

III

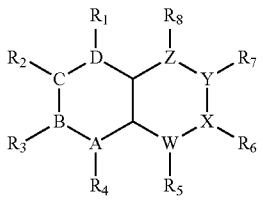

IV where A, B, C, D and W, X, Y and Z in the ring moieties is C, O, N, P, or S.

$R_1$, $R_2$, $R_3$, $R_4$, $R_5$, $R_6$, $R_7$ and $R_8$ are each independently H, alkyl or substituted alkyl, alkenyl or substituted alkenyl, alkoxy or substituted alkoxy, hydroxyl or substituted hydroxyl, amino or substituted amino, thio or substituted thio, sulfonyl or substituted sulfonyl, sulfinyl or substituted sulfinyl, sulfonylamino or substituted sulfonylamino, halo, $SO_3H$, amine, CN, $CF_3$, acyl or substituted acyl, aryl or substituted aryl, heterocyclyl or substituted heterocyclyl, alkoxy or substituted alkoxy, aldehyde or substituted aldehyde or substituted phosphine; $COR^a$, $CSR^a$ and $CONHR^a$ where $R^a$ is H, alkyl or substituted alkyl, alkenyl or substituted alkenyl, hydroxyl or substituted hydroxyl, aryl or substituted aryl, optionally heterocyclyl ring or substituted heterocyclyl ring; $OR^b$, $SR^b$ or $NR^bR^c$ where $R^b$ and $R^c$ are H or independently each other, alkyl or substituted alkyl, alkenyl or substituted alkenyl, acyl or substituted acyl, heterocyclyl ring or substituted heterocyclyl ring, CN; $C_1$ to $C_4NR^dR^e$, $HCNNR^dR^e$ or $HCNOR^d$ where $R^d$ and $R^e$ are H or independently each other, alkyl or substituted alkyl, alkenyl or substituted alkenyl, acyl or substituted acyl, heterocyclyl ring or substituted heterocyclyl ring; $SR^f$, $OR^f$ or $NR^fR^g$, where $R^f$ and $R^g$ are H or independently each other, alkyl or substituted alkyl, alkenyl or substituted alkenyl, acyl or substituted acyl, heterocyclyl ring or substituted heterocyclyl ring; $SO_2NR^hR^i$ where $R^h$ and $R^i$ are H or independently each other, alkyl or substituted alkyl, alkenyl or substituted alkenyl, acyl or substituted acyl, heterocyclyl ring or substituted heterocyclyl ring.

Preferably, the aforementioned A, B, C, D, W, X, Y and Z is each independently C or N. More preferably, the quinoline derivative of the present invention is the following formula:

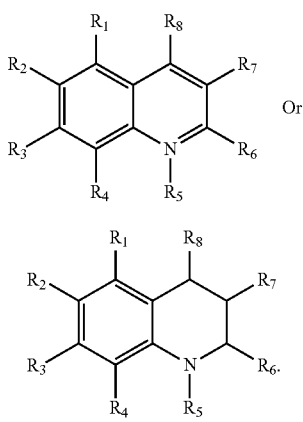

formula B

Or formula A wherein $R_1$, $R_2$ and $R_3$ are each independently H or Br; $R_5$, $R_7$ and $R_8$ are H; $R_6$ is selected from the group consisting of $CH_3$, $CH_2CH_3$, OBn, $CH_2CH_2Ph$, $CH_2OH$; and $R_4$ is a substituted phenyl group, OBn, OH or OAc wherein said phenyl group is of the following formula:

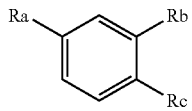

wherein Ra is $COH_2$, Rb is H, and Rc is Ph, F, Cl, $OCF_3$, $CF_3$, CN, OMe or $NO_2$; or Ra is $COH_2$, Rb is Ph, F, Cl, $OCF_3$, CN, OMe or $NO_2$, and Rc is H.

The various features of novelty which characterize the invention are pointed out with claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF THE INVENTION

Figure 1:
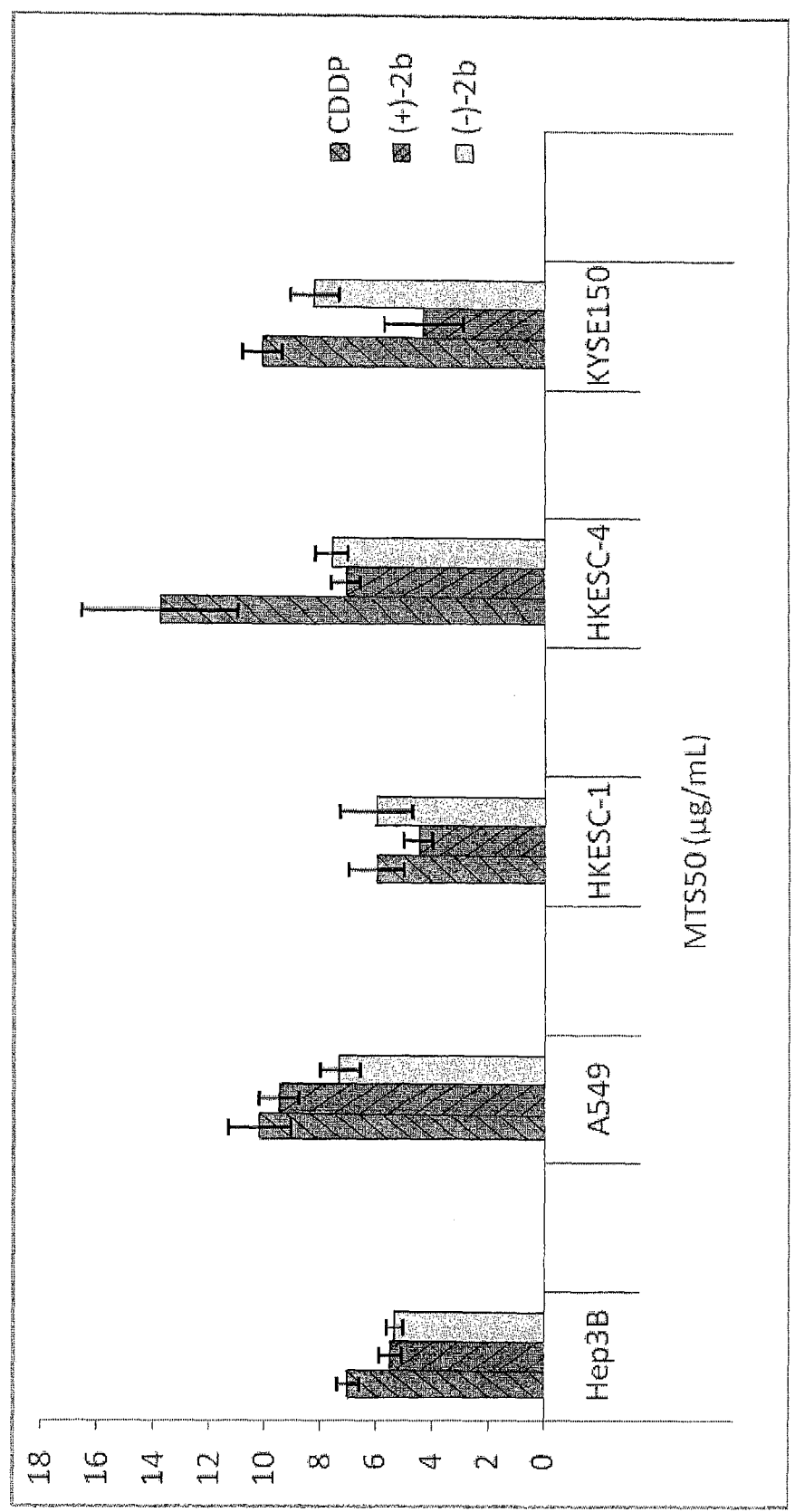
FIG. 1 shows the results of the MTS assays for compounds (+)-2b and (−)-2b on the carcinoma cell lines compared with CDDP

The term "alkyl or substituted alkyl" denotes such radicals as straight chain, branched chain or cyclic hydrocarbon groups with 1 to 10 carbon atoms. These alkyl groups are methyl, ethyl, propyl, isopropyl, butyl, isobutyl, sec-butyl, tert-butyl, pentyl, hexyl, heptyl, octyl, nonyl, decyl, cyclopropyl, cyclobutyl, cyclopentyl or cyclohexyl.

The term "alkenyl or substituted alkenyl" denotes such radicals as straight chain, branched chain or cyclic hydrocarbon groups with at least one C═C double bond. These alkenyl groups are vinyl, allyl, propenyl, butenyl, 2-butenyl, 3-butenyl, 1-pentenyl, 2-pentenyl, 3-pentenyl, 4-pentenyl, cyclopentenyl, 1-methyl-cyclopentenyl, 1-hexenyl, 2-hexenyl, 3-hexenyl, 4-hexenyl, 5-hexenyl, cyclohexenyl, 1-heptenyl, 2-heptenyl, 3-heptenyl, 4-heptenyl, 5-heptenyl, 6-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, as well as the straight and branched chain of the trienes.

The term "acyl or substituted acyl" denotes such radicals as aromatic, aliphatic or heterocyclic acyl group, the example the acyl groups are carbamoyl, straight or branch chain alkanoyl, such as, formyl, acetyl, propanoyl, butanoyl, isopropanoyl, pentanoyl, hexnoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl; alkoxycarbonyl, such as, methoxycarbonyl, ethoxycarbonyl, tetr-butoxycarbonyl, tetr-pentyloxycarbonyl or heptyloxycarbonyl; cycloalkylcarbonyl, such as, cyclopropylcarbonyl, cyclobutylcarbonyl, cyclopentyl, carbonyl or cyclohexylcarbonyl; alkylsulfonyl, such as, methylsulfonyl or ethylsulfonyl; alkoxysulfonyl, such as, methoxysulfonyl or ethoxysulfonyl; aroyl, such as, benxoyl, toluoyl or naphthoyl; aralkanoyl, such as, phenylacetyl, phenylpropanoyl, phenylbutanoyl, phenylisobutyl, phenylpentanoyl, phenylhexanoyl, naphthylacetyl, naphthylpropanoyl, naphthylbutanoyl; aralkenoyl, such as, phenylpropenoyl, phenylpentenoyl, phenylhexenoyl, naphthylpropenoyl, naphthylbutenoyl, naphthylpentenoyl; aralkoxycarbonyl, such as, benzyloxycarbonyl; aryloxycarbonyl, such as, phenoxyacetyl, naphthyloxycarbonyl; aryloxyalkanoyl, such as, phenoxyacetyl, phenoxypropionyl; arycarbamoyl, such as, phenylcarbamoyl, arylthiocarbamoyl, such as, phenylthiocarbamoyl; arylglyoxyloyl, such as, phenylglyoxyloyl, naphthylglyoxyloyl; arylsulfonyl, such as, phenylsulfonyl, naphthylsulfonyl; heterocycliccarbonyl, heterocylclicalkanoyl, such as, thienylacetyl, thienylpropanoyl, thienylbutanoyl, thienylpentanoyl, thienylhexanoyl, thiazolylacetyl, thiadiazolylacetyl, or tetrazolylacetyl, heterocyclicalkenoyl, such as, heterocyclicpropenoyl, heterocyclicbutenoyl, heterocyclicpentenoyl or heterocyclichexenoyl or heterocyclicglyoxyloyl, such as, thiazolylglyoxyloyl thienyglyoxyloyl.

The term "aryl or substituted aryl" denotes such radicals as carbocyclic aromatic or heterocyclic aromatic system, such as, phenyl, naphthyl, tetrahydronaphthyl, indane or biphenyl. These systems may be unsubstituted of substituted by one or more groups, such as, halogen, haloalkyl, hydroxyl, alkoxy, carbonyl, amido, alkylamido, dialkylamido, nitro, amino, alkylamino, dialkylamino, carboxy, thio or thioalkyl.

The term "heterocyclyl ring or substituted heterocyclyl ring" refers to monocyclic or polycyclic heterocyclic groups containing at least one heteroatom, such as, N-containing saturated and unsaturated heterocyclic groups, for example, pyrrolidinyl, imidazolidinyl, piperidino, piperazinyl; pyrrolyl, pyrrolinyl, imidazolyl, pyrazolyl, pyridyl, pyrimidinyl, pyrazinyl, pyridazinyl, triazolyl, tetrazolyl; indolyl, isoindolyl, indolizinyl, benzimidazolyl, quinolyl, isoquinolyl, indazolyl, benzotriazolyl or tetrazolopyridazinyl; O-containing saturated and unsaturated heterocyclic groups, for example, pyranyl, furyl, oxazolyl, isoxazolyl, oxadiazolyl, morpholinyl, benzoxazolyl or benzoxadiazolyl; S-containing saturated and unsaturated heterocyclic groups, for example, thienyl, thiazolyl, thiadiazolyl, thiazolidinyl or thiazolidinyl.

The term "halo or halogen" refer to fluorine, chlorine, bromine or iodine atom which can be one or more halogen atoms.

The term "hydroxyl" refers to a hydrogen bond to an oxygen atom, the term "substituted hydroxyl" denotes a hydroxyl group substituted with one or more groups, such as, halogen, protected hydroxyl, cyano, nitro, alkyl or substituted alkyl, alkenyl or substituted alkenyl, acyl or substituted acyl, awl or substituted awl, heterocyclyl ring or substituted heterocyclyl ring, alkoxy or substituted alkoxy, acyloxy or substituted acyloxy, carboxy or protected carboxy, carboxymethyl or protected carboxymethyl, hydroxymethyl or protected hydroxymethyl, amino or protected amino, carboxamide or protected carboxamide.

The term "alkoxy or substituted alkoxy" refers to straight or branch chain oxo-containing atoms with alkyl, for example, methoxy, ethoxy, propoxy, butoxy, and tert-butoxy.

The term "thio or substituted thio" refers to radicals containing —SH or —S— group, for examples, methylthio, ethylthio, propylthio, butylthio, hexylthio.

The term "sulfonyl or substituted sulfonyl" refers to radicals containing —S(O)$_2$— group, for examples, methylsulfonyl, ethylsulfonyl, propylsulfonyl, trifluoromethanesulfonyl, trichloromethanesulfonyl or other halogen-substituted alky- or aryl-sulfonyl.

The term "sulfinyl or substituted sulfinyl" refers to radicals containing —S(=O)-group, for examples, methylsulfinyl, ethylsulfinyl, butylsulfinyl, hexylsulfinyl.

Synthesis of Substituted Quinoline

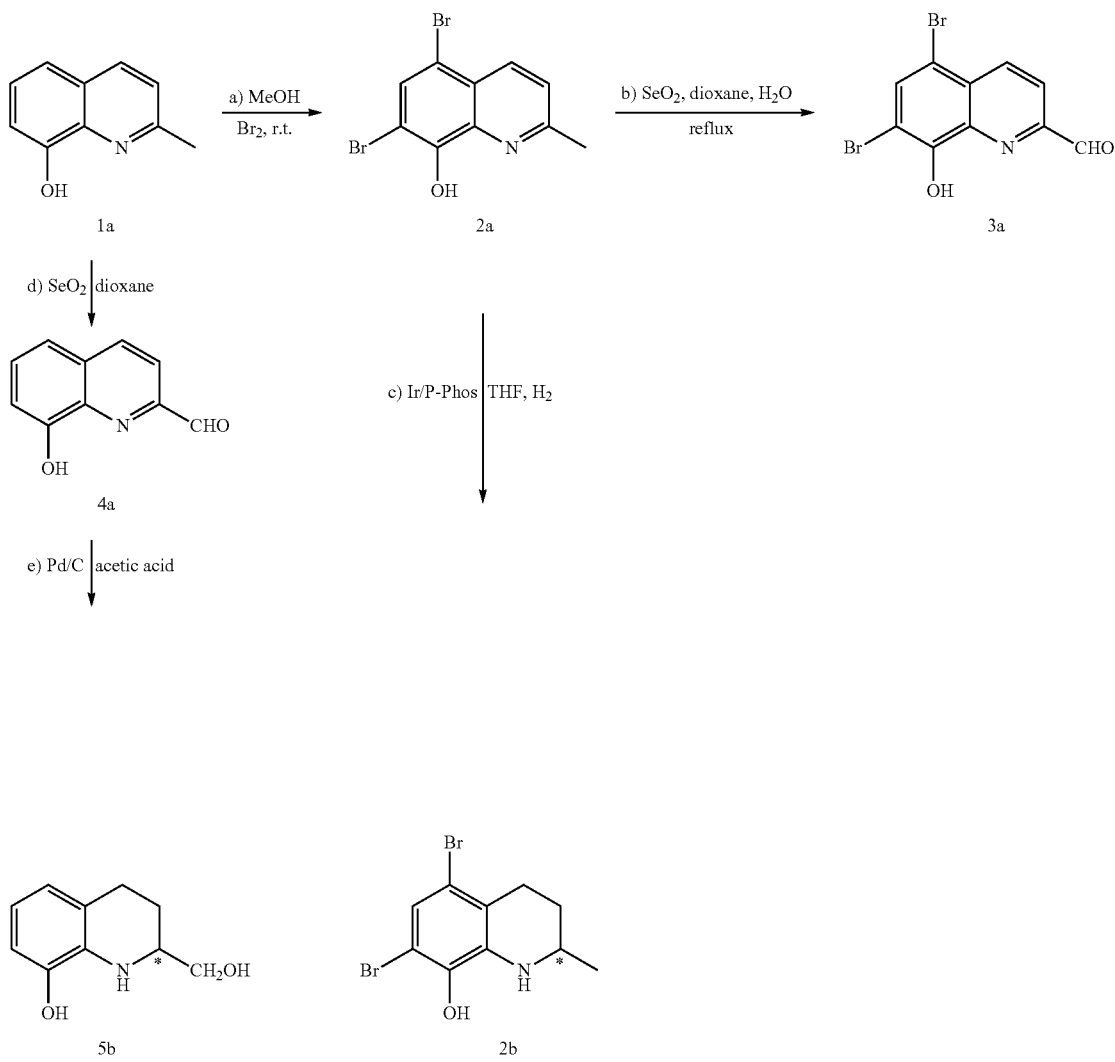

a) 5,7-Dibromo-2-methylquinolin-8-ol (2a)

2-methyl-8-quinolinol 1a (1.6 g, 10 mmol) was dissolved in 150 mL MeOH. 1 ml $Br_2$ in MeOH was added into the solution dropwise. After completed reaction, $Na_2SO_3$ was added and the product was extracted by DCM to give the crude product. The crude product was purified by silica gel column chromatography to give the pure product, $^1$H-NMR (500 MHz, $CDCl_3$): δ 2.75 (s, 3H), 7.39 (d, 1H, J=8.5 Hz), 7.79 (s, 1H), 8.26 (d, 1H, J=8.5 Hz); $^{13}$C-NMR (125 MHz, $CDCl_3$): δ 25.40, 104.23, 110.64, 124.60, 125.47, 133.30, 136.64, 138.63, 149.76, 159.46; HRMS (ESI): Calcd. for $C_{10}H_8NOBr_2$ [M+H]$^+$, 315.8973. found 315.8981. Yield=64.4%.

b) 5,7-Dibromo-8-hydroxyquinoline-2-carbaldehyde (3a)

5,7-Dibromo-2-methylquinolin-8-ol 2a (950 mg, 3 mmol), selenium dioxide (418 mg, 3.8 mmol), 100 ml of pre-dried 1,4-dioxane, and 0.5 ml of water were mixed and stirred in a 500 mL round bottom flask. The resulting solution was refluxed for 24 h and the reaction was monitored until completion using TLC method. Then the mixture was filtered off, and the selenium metal was washed with DCM, and the combined filtrates were evaporated off under reduced pressure, the crude product was purified by silica gel chromatography to yield the pure product, $^1$H-NMR (500 MHz, $CDCl_3$): δ 8.06 (s, 1H), 8.17 (d, 1H, J=8.5 Hz), 8.64 (d, 1H, J=8.5 Hz), 10.25 (s, 1H); $^{13}$C-NMR (125 MHz, $CDCl_3$): δ 106.02, 111.08, 119.83, 129.23, 137.30, 138.63, 138.78, 150.97, 151.72, 192.32; HRMS (ESI): Calcd. for $C_{10}H_6NO_2Br_2$ [M+H]$^+$, 329.8765. found 329.8765. Yield=98.0%.

c) 5,7-Dibromo-1,2,3,4-tetrahydro-2-methylquinolin-8-ol (2b)

A mixture of $[Ir(COD)Cl]_2$ (1.0 mg, 0.0015 mmol) and the P-Phos (2.1 mg, 0.0032 mmol) or other $C_2$-symmetric bidendate chiral diphosphines ligands in dried solvent (e.g. THF) (1.0 mL) was stirred at room temperature for 30 minutes in a glovebox. The mixture was transferred by a syringe to stainless steel autoclave, in which $I_2$ (4 mg, 0.015 mmol) and 5,7-dibromo-2-methylquinolin-8-ol 2a (95 mg, 0.3 mmol) in 0.5 mL dried solvent were placed beforehand. The hydrogenation was performed at room temperature under $H_2$ for 20 h. After carefully releasing the hydrogen, the reaction mixture was quenched with saturated sodium carbonate solution (2.0 mL) for 15 minutes. The aqueous layer was extracted with EA (3×3 mL). The combined organic layer was dried with sodium sulfate and concentrated in vacuo to give the crude product. Purification by a silica gel column eluted with hexane/EA gave the pure product. The enantiomeric excesses (ee) were determined by HPLC with chiral column, $^1$H-NMR (500 MHz, $CDCl_3$): δ 1.26 (d, 3H, J=6.0 Hz), 1.53-1.61 (m, 1H), 1.96-2.01 (m, 1H), 2.59-2.66 (m, 1H), 2.80-2.85 (m, 1H), 3.35-3.39 (m, 1H), 6.96 (s, 1H); $^{13}$C-NMR (125 MHz, $CDCl_3$): δ 22.75, 27.89, 30.17, 46.90, 107.32, 116.76, 120.83, 120.97, 135.93, 138.33; HRMS (ESI): Calcd. for $C_{10}H_{12}NOBr_2$ [M+H]$^+$, 319.9286. found 319.9261. HPLC (OJ-H, elute: Hexanes/i-PrOH=99/1, detector: 254 nm, flow rate: 1.0 mL/min), (S)=$t_1$=19.08 min, (R) $t_2$=20.45 min.

Optical pure 5,7-Dibromo-1,2,3,4-tetrahydro-2-methylquinolin-8-ol (+)-(2b)/(−)-(2b) was prepared by preparative HPLC with daicel OJ-H chiral preparative column (elute: Hexanes/i-PrOH=95/5, detector: 254 nm, flow rate: 5.0 mL/min), (S) $t_1$=37.6 min, (R) $t_2$=43.8 min.

d) 8-Hydroxy-2-quinolinecarboxaldehyde (4a)

8-Hydroxy-2-methylquinoline 1a (12.4 mmol, 1.97 g), selenium dioxide (15.8 mmol, 1.74 g), 300 ml of pre-dried 1,4-dioxane, and 1.5 ml of water were mixed and stirred in a 1-L round bottom flask. The resulting solution was refluxed for 24 h. The workup procedure can refer to step (b) in order to obtain pure, $^1$H-NMR (500 MHz, $C_6D_6$): δ 6.76-6.79 (m, 1H), 7.05 (d, 1H, J=4.0 Hz), 7.12 (s, 1H), 7.33 (d, 1H, J=9.0 Hz), 7.63 (d, 1H, J=9.0 Hz), 8.02 (s, 1H), 9.79 (s, 1H); $^{13}$C-NMR (125 MHz, $C_6D_6$): δ 111.81, 118.33, 118.49, 130.98, 131.35, 137.81, 138.54, 150.99, 154.19, 192.58; LRMS (ESI): 174.05 [M+H]$^+$; Melting point: 99.7° C.

e) 1,2,3,4-Tetrahydro-2-(hydroxymethyl)quinolin-8-ol (5b)

A mixture of 10% Pd/C (500 mg), 8-hydroxy-2-quinolinecarboxaldehyde (500 mg, 2.89 mmol), and acetic acid (10 ml) was stirred in an autoclave under 100 bar hydrogen pressure at room temperature for 20 h. The mixture was filtered through a short pad of Celite, which was subsequently washed with MeOH (20 ml). Hydrochloric acid was added, and the solvent was removed under reduced pressure to give the crude product. Purification by a silica gel column eluted with hexane/EA gave the pure product, $^1$H-NMR (500 MHz, $CDCl_3$): δ 1.60-1.67 (m, 1H), 1.92-1.98 (m, 1H), 2.71-2.80 (m, 1H), 2.81-2.87 (m, 1H), 3.51-3.54 (m, 1H), 3.66-3.69 (m, 1H), 6.45-6.54 (m, 3H); $^{13}$C-NMR (125 MHz, $CDCl_3$): δ 26.75, 27.59, 55.11, 67.92, 113.52, 119.16, 122.14, 124.57, 134.98, 146.30; HRMS (ESI): Calcd. for $C_{10}H_{11}NO_2Na$ [M+Na]$^+$, 200.0687. found 200.0685.

Synthesis of Alkoxy-Substituted Quinaldine

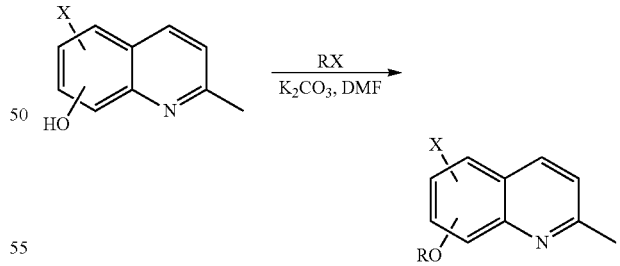

To a solution of hydroxyl-substituted halogenated or non-halogenated quinoline (3 mmol), alkyl halide (RX, 3 mmol, where X=Br$^-$ or Cl) and $K_2CO_3$ were stirred in 10 mL DMF. The reaction was run at room temperature and monitored by TLC. After the reaction was complete, the mixture was washed with $Na_2CO_3$ and extracted with EA and then dried over anhydrous sodium sulfate. Then the solvent was removed under reduced pressure and the crude product was purified by silica gel column chromatography to give the pure product.

6-Propoxyquinoline (6a)

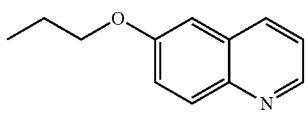

$^1$H-NMR (500 MHz, CDCl$_3$): δ1.03 (t, 3H, J=7.5 Hz), 1.79-1.86 (m, 2H), 3.96 (t, 2H, J=6.5 Hz), 6.98 (d, 1H, J=2.5 Hz), 7.25-7.27 (m, 1H), 7.31-7.34 (m, 1H), 7.94-7.96 (m, 2H), 8.70-8.71 (m, 1H); $^{13}$C-NMR (125 MHz, CDCl$_3$): δ 11.12, 23.07, 70.31, 106.37, 121.82, 123.10, 129.89, 131.33, 135.23, 144.92, 148.36, 157.79; Yield=82.6%.

6-Butoxyquinoline (7a)

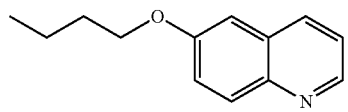

$^1$H-NMR (500 MHz, CDCl$_3$): δ 0.96 (t, 3H, J=7.5 Hz), 1.47-1.51 (m, 2H), 1.76-1.81 (m, 2H), 4.00 (t, 2H, J=7.0 Hz), 6.99 (d, 1H, J=3.0 Hz), 7.25-7.27 (m, 1H), 7.31-7.34 (m, 1H), 7.94-7.97 (m, 2H), 8.70-8.71 (m, 1H); $^{13}$C-NMR (125 MHz, CDCl$_3$): δ 14.42, 19.85, 31.78, 68.52, 106.35, 121.82, 123.12, 129.90, 131.33, 135.23, 144.93, 148.36, 157.81; Yield=93.7%.

8-(2-(Piperidin-1-yl)ethoxy)-2-methylquinoline (8a)

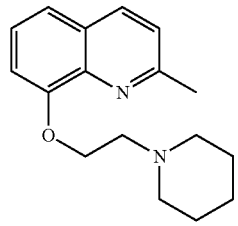 [SMILES: Cc1ccc2cccc(OCCN3CCCCC3)c2n1]

$^1$H-NMR (500 MHz, CDCl$_3$): δ 1.46 (bs, 2H), 1.70 (bs, 4H), 2.71 (bs, 7H), 3.04 (bs, 2H), 4.34 (bs, 2H), 6.99 (d, 1H, J=7.0 Hz), 7.24 (d, 1H, J=9.0 Hz), 7.28-7.33 (m, 2H), 7.95 (d, 1H, J=8.5 Hz); $^{13}$C-NMR (125 MHz, CDCl$_3$): δ 23.81, 24.88, 25.31, 54.46, 57.31, 64.31, 109.36, 120.26, 122.95, 125.94, 127.98, 136.58, 139.62, 153.83, 158.46; LRMS (ESI): 271.21 [M+H]$^+$

8-(3-nitrobenzyloxy)-2-methylquinoline (9a)

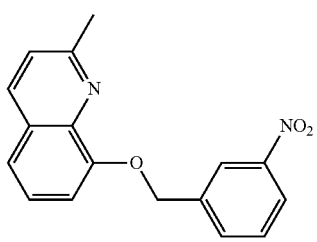 [SMILES: Cc1ccc2cccc(OCc3cccc([N+](=O)[O-])c3)c2n1]

$^1$H-NMR (500 MHz, CDCl$_3$): δ 2.82 (s, 3H), 5.52 (s, 2H), 7.00 (d, 1H, J=7.5 Hz), 7.32 (q, 2H, J=9.0 Hz), 7.39 (d, 1H, J=8.0 Hz), 7.54 (t, 1H, J=7.5 Hz), 7.89 (d, 1H, J=7.5 Hz), 8.02 (d, 1H, J=8.5 Hz), 8.16 (d, 1H, J=8.5 Hz), 8.44 (s, 1H); $^{13}$C-NMR (125 MHz, CDCl$_3$): δ 26.45, 70.59, 111.57, 121.40, 122.60, 123.41, 126.07, 128.52, 130.22, 133.57, 136.78, 140.26, 140.73, 149.11, 154.02, 159.18; HRMS (ESI): Calcd. for C$_{17}$H$_{15}$N$_2$O$_3$ [M+H]$^+$, 295.1083. found 295.1078. Melting Point=94.4-95.2° C.; Yield=80.1%.

8-(4-nitrobenzyloxy)-2-methylquinoline (10a)

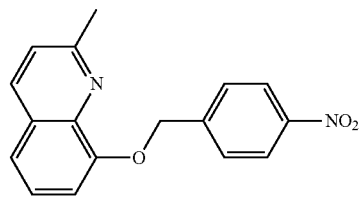 [SMILES: Cc1ccc2cccc(OCc3ccc([N+](=O)[O-])cc3)c2n1]

$^1$H-NMR (500 MHz, CDCl$_3$): δ 2.81 (s, 3H), 5.53 (s, 2H), 6.94 (d, 1H, J=7.5 Hz), 7.26-7.39 (m, 3H), 7.69 (d, 2H, J=8.5 Hz), 8.02 (d, 1H, J=8.5 Hz), 8.22 (d, 2H, J=9.0 Hz); $^{13}$C-NMR (125 MHz, CDCl$_3$): δ 26.40, 70.34, 111.18, 121.26, 123.38, 124.42, 125.60, 127.89, 128.46, 136.76, 140.56, 145.49, 148.05, 153.82, 159.10; HRMS (ESI): Calcd. for C$_{17}$H$_{15}$N$_2$O$_3$ [M+H]$^+$, 295.1083. found 295.1089. Melting Point=144.1-145.7° C.; Yield=50%.

8-(4-methoxybenzyloxy)-2-methylquinoline (11a)

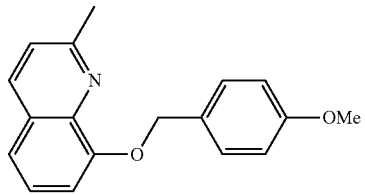 [SMILES: COc1ccc(COc2cccc3ccc(C)nc23)cc1]

$^1$H-NMR (500 MHz, CDCl$_3$): δ 2.80 (s, 3H), 3.80 (s, 3H), 5.38 (s, 2H), 6.90 (d, 2H, J=8.0 Hz), 7.03 (d, 1H, J=7.0 Hz), 7.26-7.34 (m, 3H), 7.45 (d, 2H, J=8.5 Hz), 8.00 (d, 1H, J=8.5 Hz); $^{13}$C-NMR (125 MHz, CDCl$_3$): δ 25.95, 55.50, 70.86, 110.71, 114.18, 119.98, 122.75, 125.78, 127.96, 128.89, 129.46, 136.31, 140.32, 154.15, 158.36, 159.45; HRMS (ESI): Calcd. for C$_{18}$H$_{18}$NO$_2$ [M+H]$^+$, 280.1338. found 280.1343. Melting Point=130.8-131.5° C.; Yield=67.3%.

8-(3-methoxybenzyloxy)-2-methylquinoline (12a)

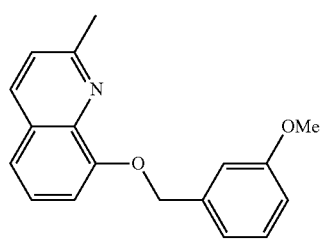 [SMILES: COc1cccc(COc2cccc3ccc(C)nc23)c1]

¹H-NMR (500 MHz, CDCl₃): δ 2.81 (s, 3H), 3.79 (s, 3H), 5.44 (s, 2H), 6.84 (d, 1H, J=8.0 Hz), 7.01 (d, 1H, J=8.0 Hz), 7.08-7.11 (m, 2H), 7.15-7.38 (m, 4H), 8.01 (d, 1H, J=8.0 Hz); ¹³C-NMR (125 MHz, CDCl₃): δ 26.42, 55.90, 71.43, 111.20, 112.85, 113.99, 119.71, 120.53, 123.21, 126.21, 128.39, 130.25, 136.74, 139.67, 140.73, 154.52, 158.81, 160.53; HRMS (ESI): Calcd. for $C_{18}H_{18}NO_2$ [M+H]⁺, 280.1338. found 280.1337. Melting Point=104.1-104.8° C.; Yield=86%.

4-((2-methylquinolin-8-yloxy)methyl)benzonitrile (13a)

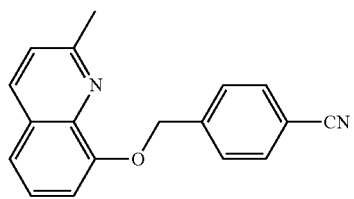 [SMILES: Cc1ccc2cccc(OCc3ccc(C#N)cc3)c2n1]

¹H-NMR (500 MHz, CDCl₃): δ 2.81 (s, 3H), 5.49 (s, 2H), 6.93 (d, 1H, J=8.0 Hz), 7.28-7.39 (m, 3H), 7.63-7.67 (m, 4H), 8.03 (d, 1H, J=8.5 Hz); ¹³C-NMR (125 MHz, CDCl₃): δ 26.03, 45.01, 70.15, 110.75, 111.72, 119.02, 120.80, 123.00, 125.64, 127.47, 128.08, 132.65, 136.39, 140.20, 143.09, 153.51, 158.71; HRMS (ESI): Calcd. for $C_{18}H_{15}N_2O$ [M+H]⁺, 275.1184. found 275.1187. Melting Point=124.1-125.3° C.; Yield=85.7%.

8-(biphenyl-3-ylmethoxy)-2-methylquinoline (14a)

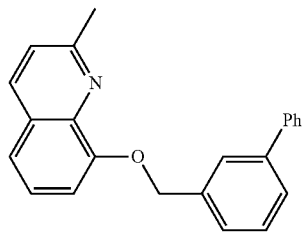 [SMILES: Cc1ccc2cccc(OCc3cccc(-c4ccccc4)c3)c2n1]

¹H-NMR (500 MHz, CDCl₃): δ 2.82 (s, 3H), 5.53 (s, 2H), 7.05 (d, 1H, J=7.5 Hz), 7.26-7.35 (m, 4H), 7.41-7.46 (m, 3H), 7.50-7.54 (m, 2H), 7.59-7.61 (m, 2H), 7.78 (s, 1H), 8.01 (d, 1H, J=8.0 Hz); ¹³C-NMR (125 MHz, CDCl₃): δ 26.01, 71.24, 110.87, 120.18, 122.81, 125.80, 125.92, 126.08, 126.74, 127.46, 127.58, 128.00, 128.96, 129.24, 136.33, 138.12, 141.20, 141.72, 154.15, 158.43; HRMS (ESI): Calcd. for $C_{23}H_{20}NO$ [M+H]⁺, 326.1545. found 326.1557. Melting Point=89.8-99.4° C.; Yield=85.7%.

8-(4-(trifluoromethoxy)benzyloxy)-2-methylquinoline (15a)

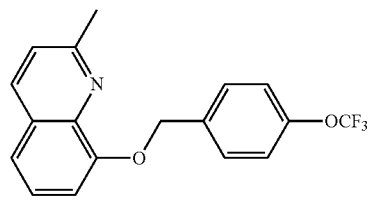 [SMILES: Cc1ccc2cccc(OCc3ccc(OC(F)(F)F)cc3)c2n1]

¹H-NMR (500 MHz, CDCl₃): δ 2.81 (s, 3H), 5.43 (s, 2H), 6.99 (d, 1H, J=6.5 Hz), 7.22 (d, 2H, J=7.5 Hz), 7.29-7.37 (m, 3H), 7.56 (d, 2H, J=9.0 Hz), 8.01 (d, 1H, J=8.5 Hz); ¹³C-NMR (125 MHz, CDCl₃): δ 26.00, 70.28, 110.72, 119.68, 120.43, 121.30, 121.31, 121.72, 122.88, 125.71, 128.02, 128.62, 136.21, 136.34, 140.26, 148.91, 153.84, 158.56; HRMS (ESI): Calcd. for $C_{18}H_{15}NO_2F_3$ [M+H]⁺, 334.1055. found 334.1056. Melting Point=103.9-104.6° C.; Yield=73.1%.

8-(4-fluorobenzyloxy)-2-methylquinoline (16a)

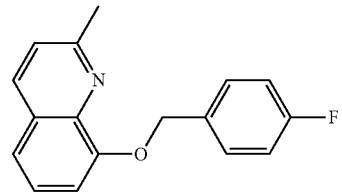 [SMILES: Cc1ccc2cccc(OCc3ccc(F)cc3)c2n1]

¹H-NMR (500 MHz, CDCl₃): δ 2.80 (s, 3H), 5.40 (s, 2H), 6.99 (d, 1H, J=6.5 Hz), 7.05 (t, 2H, J=6.5 Hz), 7.28-7.36 (m, 3H), 7.48-7.51 (m, 2H), 8.01 (d, 1H, J=8.5 Hz); ¹³C-NMR (125 MHz, CDCl₃): δ 25.98, 70.47, 110.75, 115.59, 115.76, 120.29, 122.83, 125.72, 128.00, 129.02, 129.09, 133.17, 136.33, 140.28, 153.92, 158.48, 161.61, 163.56; HRMS (ESI): Calcd. for $C_{17}H_{15}NOF$ [M+H]⁺, 268.1138. found 268.1144. Melting Point=130-130.6° C.; Yield=80.5%.

8-(4-(trifluoromethyl)benzyloxy)-2-methylquinoline (17a)

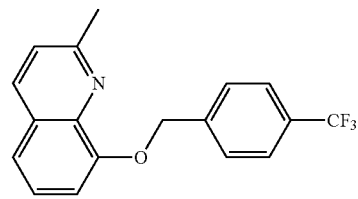 [SMILES: Cc1ccc2cccc(OCc3ccc(C(F)(F)F)cc3)c2n1]

¹H-NMR (500 MHz, CDCl₃): δ 2.82 (s, 3H), 5.50 (s, 2H), 6.95 (d, 1H, J=8.0 Hz), 7.26-7.37 (m, 3H), 7.61-7.65 (m, 4H), 8.02 (d, 1H, J=8.5 Hz); ¹³C-NMR (125 MHz, CDCl₃): δ 26.01, 70.30, 110.72, 120.55, 122.55, 125.62, 127.16, 128.05, 130.09, 136.37, 140.23, 141.65, 153.69, 158.62; HRMS (ESI): Calcd. for $C_{18}H_{15}NOF_3$ [M+H]⁺, 318.1106. found 318.1118. Melting Point=130.8-131.5° C.; Yield=82%.

8-(4-chlorobenzyloxy)-2-methylquinoline (18a)

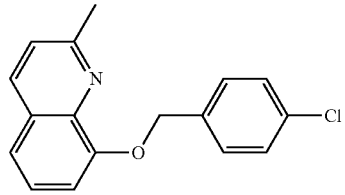 [SMILES: Cc1ccc2cccc(OCc3ccc(Cl)cc3)c2n1]

¹H-NMR (500 MHz, CDCl₃): δ 2.80 (s, 3H), 5.41 (s, 2H), 6.96 (d, 1H, J=6.5 Hz), 7.27-7.36 (m, 5H), 7.45 (d, 2H, J=8.5 Hz), 8.01 (d, 1H, J=8.5 Hz); ¹³C-NMR (125 MHz, CDCl₃): δ 26.01, 70.35, 110.76, 120.36, 122.86, 125.70, 128.01, 128.52, 128.96, 133.64, 136.01, 136.34, 140.27, 153.82, 158.52; HRMS (ESI): Calcd. for $C_{17}H_{15}NOCl$ [M+H]⁺, 284.0842. found 284.0841. Melting Point=118.7-119° C.; Yield=90.5%.

2-Methylquinolin-8-yl(7,7-dimethyl-2-oxobicyclo[2.2.1]heptan-1-yl)methanesulfonate (19a)

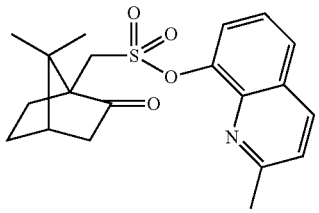 [SMILES: Cc1ccc2cccc(OS(=O)(=O)CC34CCC(CC3=O)C4(C)C)c2n1]

$^1$H-NMR (500 MHz, CDCl$_3$): δ 0.95 (s, 3H), 1.19 (s, 3H), 1.41-1.47 (m, 1H), 1.70-1.76 (m, 1H), 1.95 (d, 1H, J=18.5 Hz), 2.05-2.13 (m, 2H), 2.39-2.44 (m, 1H), 2.57-2.63 (m, 1H), 2.77 (s, 3H), 3.91 (d, 1H, J=15.5 Hz), 4.44 (d, 1H, J=15.0 Hz), 7.35 (d, 1H, J=8.5 Hz), 7.48 (t, 1H, J=8.0 Hz), 7.67 (d, 1H, J=7.5 Hz), 7.73 (d, 1H, J=8.0 Hz), 8.08 (d, 1H, J=8.5 Hz); $^{13}$C-NMR (125 MHz, CDCl$_3$): δ 19.99, 20.32, 25.42, 25.66, 27.16, 42.75, 43.20, 48.12, 49.71, 58.68, 123.18, 123.92, 125.60, 127.00, 128.37, 136.42, 141.24, 145.50, 160.15, 214.64; HRMS (ESI): 374.1438 [M+H]$^+$; Yield=65%.

1-(4-fluorophenyl)-2-(2-methylquinolin-8-yloxy)ethanone (20a)

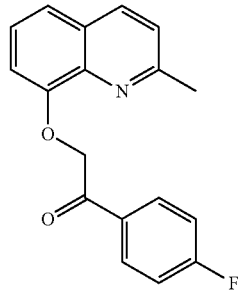 [SMILES: Cc1ccc2cccc(OCC(=O)c3ccc(F)cc3)c2n1]

$^1$H-NMR (500 MHz, CDCl$_3$): δ 2.77 (s, 3H), 5.56 (s, 2H), 6.97 (d, 1H, J=7.5 Hz), 7.15 (t, 2H, J=8.5 Hz), 7.32 (t, 2H, J=7.5 Hz), 7.39 (d, 1H, J=8.0 Hz); 8.01 (d, 1H, J=8.0 Hz), 8.18-8.21 (m, 2H); $^{13}$C-NMR (125 MHz, CDCl$_3$): δ 26.17, 72.88, 105.32, 111.38, 116.51, 121.49, 123.24, 125.94, 128.44, 131.77, 136.67, 140.37, 153.77, 158.88, 165.64, 167.68, 193.97; HRMS (ESI): Calcd. for C$_{18}$H$_{15}$NO$_2$F [M+H]$^+$, 296.1087. found 296.1090. Yield=77.7%.

5,7-Dibromo-8-ethoxy-2-methylquinoline (21a)

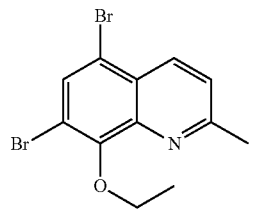 [SMILES: CCOc1c(Br)cc(Br)c2ccc(C)nc12]

$^1$H-NMR (500 MHz, CDCl$_3$): δ 1.53 (t, 3H, J=7.0 Hz), 2.77 (s, 3H), 4.45 (q, 2H, J=7.0 Hz), 7.36 (d, 1H, J=8.5 Hz), 7.88 (s, 1H), 8.30 (d, 1H, J=8.5 Hz); $^{13}$C-NMR (125 MHz, CDCl$_3$): δ 16.45, 26.13, 71.74, 116.44, 117.24, 123.93, 126.97, 133.12, 136.54, 144.09, 152.99, 160.44; HRMS (ESI): Calcd. for C$_{12}$H$_{12}$NOBr$_2$ [M+H]$^+$, 343.9286. found 343.9288. Yield=83.5%.

2-(5,7-dibromo-2-methylquinolin-8-yloxy)-1-phenylethanone (22a)

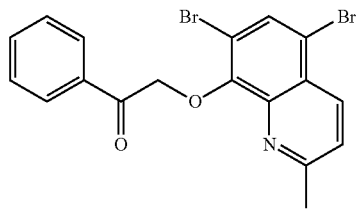 [SMILES: Cc1ccc2c(Br)cc(Br)c(OCC(=O)c3ccccc3)c2n1]

$^1$H-NMR (500 MHz, CDCl$_3$): δ 2.54 (s, 3H), 5.79 (s, 2H), 7.30 (d, 1H, J=9.0 Hz), 7.48 (t, 2H, J=8.0 Hz), 7.58 (t, 1H, J=7.0 Hz), 7.89 (s, 1H), 8.13 (d, 2H, J=8.0 Hz), 8.27 (d, 1H, J=9.0 Hz); $^{13}$C-NMR (125 MHz, CDCl$_3$): δ 25.53, 77.05, 115.78, 116.17, 123.94, 126.88, 129.04, 129.30, 133.22, 134.08, 135.67, 136.65, 142.63, 151.55, 159.92, 195.12; HRMS (ESI): Calcd. for C$_{18}$H$_{14}$NO$_2$Br$_2$ [M+H]$^+$, 433.9391. found 433.9398. Yield=87.7%.

Synthesis of 2,8-Bis(benzyloxy)quinoline and 1-Benzyl-8-(benzyloxy)quinolin-2(1H)-one

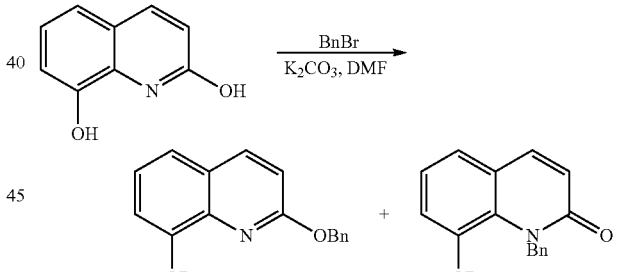

2,8-Bis(benzyloxy)quinoline (23a)

$^1$H-NMR (500 MHz, CDCl$_3$): δ 5.26 (s, 2H), 5.51 (s, 2H), 6.90 (d, 1H, J=9.0 Hz), 7.04 (d, 1H, J=8.0 Hz), 7.16-7.20 (m, 1H), 7.22-7.32 (m, 7H), 7.48 (q, 4H, J=8.0 Hz), 7.89 (d, 1H, J=9.0 Hz); $^{13}$C-NMR (125 MHz, CDCl$_3$): δ 67.96, 71.60, 112.65, 113.70, 120.58, 124.21, 126.69, 127.52, 127.99, 128.09, 128.63, 128.72, 128.90, 137.66, 137.77, 138.68, 139.19, 153.56, 161.35; LRMS (ESI): 342.07 [M+H]$^+$; Yield=53.4%.

1-Benzyl-8-(benzyloxy)quinolin-2(1H)-one (24a)

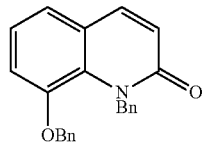 [SMILES: O=c1ccc2cccc(OCc3ccccc3)c2n1Cc1ccccc1]

$^1$H-NMR (500 MHz, CDCl$_3$): δ 4.88 (s, 2H), 5.94 (s, 2H), 6.79 (d, 1H, J=9.0 Hz), 6.90 (d, 2H, J=7.5 Hz), 7.02 (d, 1H, J=8.0 Hz), 7.06-7.19 (m, 7H), 7.26-7.31 (m, 3H), 7.69 (d, 1H, J=7.5 Hz); $^{13}$C-NMR (125 MHz, CDCl$_3$): δ 49.70, 72.05, 115.22, 122.15, 122.33, 123.07, 123.52, 125.85, 126.28, 127.82, 128.37, 128.42, 128.83, 130.95, 136.14, 139.37, 140.14, 147.49, 163.80; LRMS (ESI): 342.07 [M+H]$^+$; Yield=31.4%.

Synthesis of 1-Acetyl-2-methyl-1,2,3,4-tetrahydroquinolin-8-yl acetate and 2-Methyl-1,2,3,4-tetrahydroquinolin-8-yl acetate

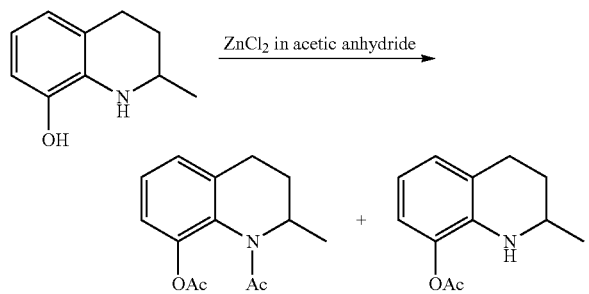

Add slowly 100 mg (0.6 mmol) of 1,2,3,4-tetrahydro-2-methylquinolin-8-ol into a preheated solution of ZnCl$_2$ (4%) (0.5 g anhydrous ZnCl$_2$ in 12.5 ml acetic anhydride) in a 50 ml round flask bottom which was attached with an air condenser. Then the mixture was heated on a water bath for another one hour. After the reaction was completed, cool the solution with cold water, and then pour into ice water (10 ml) and stir vigorously to assist the hydrolysis of unreacted acetic anhydride. Then the product was extracted with EA and dried over anhydrous sodium sulfate. The solvent was removed under reduced pressure and the crude product was purified by silica gel column chromatography to give the pure product.

2-Methyl-1,2,3,4-tetrahydroquinolin-8-yl acetate (25b)

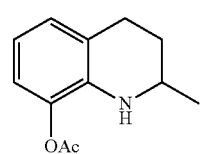

$^1$H-NMR (500 MHz, CDCl$_3$): δ 2.50 (s, 3H), 2.73 (s, 3H), 7.30 (d, 1H, J=9.0 Hz), 7.40 (d, 1H, J=7.5 Hz), 7.46 (t, 1H, J=8.0 Hz), 7.67 (d, 1H, J=8.5 Hz), 8.05 (d, 1H, J=9.0 Hz); $^{13}$C-NMR (125 MHz, CDCl$_3$): δ 21.23, 25.96, 31.15, 121.54, 122.89, 125.43, 125.80, 128.01, 136.22, 140.89, 147.24, 159.64, 170.21; LRMS (ESI): 202.09 [M+H]$^+$; Yield=91.1%.

1-Acetyl-2-methyl-1,2,3,4-tetrahydroquinolin-8-yl acetate (26b)

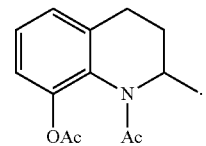

$^1$H-NMR (500 MHz, CDCl$_3$): δ 1.05 (d, 3H, J=6.5 Hz), 1.20-1.26 (m, 1H), 2.01 (s, 3H), 2.27 (s, 3H), 2.37-2.45 (m, 2H), 2.59-2.62 (m, 1H), 4.81 (q, 1H, J=7.5 Hz), 7.02 (d, 1H, J=8.5 Hz), 7.10 (d, 1H, J=7.5 Hz), 7.21 (t, 1H, J=8.0 Hz); $^{13}$C-NMR (125 MHz, CDCl$_3$): δ 20.96, 21.40, 22.19, 27.28, 33.63, 49.52, 121.59, 124.99, 126.99, 131.13, 139.60, 145.68, 168.93, 170.93; LRMS (ESI): 270.10 [M+Na]$^+$

Synthesis of 8-Benzyloxy Substituted Quinoline

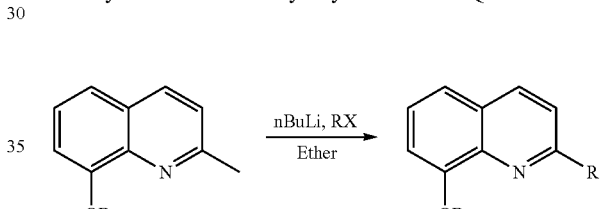

To a solution of 8-(Benzyloxy)-2-methylquinoline (3 mmol, 790 mg) in 15 mL ether was added a 1.6M solution of n-butyllithium in hexane (3.5 mmol, 2.2 mL) at 0° C. over 30 minutes. This solution was allowed to warm to room temperature and stirred for 1 h. The above mixture, a solution of BnBr (3 mmol) in 15 mL ether was added dropwise over 15 minutes with vigorous stirring while the temperature was cooled to 0° C. The mixture was then stirred overnight and hydrolysed with a saturated aqueous ammonium chloride solution. The organic layer was separated and the aqueous layer was further extracted with ether (3×50 mL). The combined organic layers were washed with brine and dried over anhydrous sodium sulfate. The solvent was removed under reduced pressure and the crude product was purified by silica gel column chromatography to give the pure product.

8-(Benzyloxy)-2-ethylquinoline (27a)

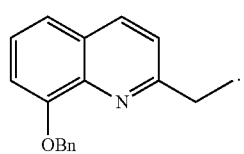 [SMILES: CCc1ccc2cccc(OCc3ccccc3)c2n1]

¹H-NMR (500 MHz, CDCl₃): δ 1.43 (t, 3H, J=7.5 Hz), 3.10 (q, 2H, J=7.5 Hz), 5.47 (s, 2H), 7.02 (d, 1H, J=7.5 Hz), 7.30 (t, 2H, J=7.5 Hz), 7.36 (t, 4H, J=8.0 Hz), 7.54 (d, 2H, J=7.5 Hz), 8.04 (d, 1H, J=8.5 Hz); ¹³C-NMR (125 MHz, CDCl₃): δ14.32, 32.62, 71.17, 110.97, 120.18, 121.49, 125.79, 127.18, 127.87, 128.24, 128.76, 136.47, 137.59, 140.32, 154.25, 163.34; LRMS (ESI): 264.10 [M+H]⁺.

8-(Benzyloxy)-2-phenethylquinoline (28a)

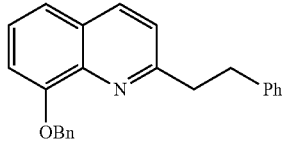 [SMILES: c1ccc(CCc2ccc3cccc(OCc4ccccc4)c3n2)cc1]

¹H-NMR (500 MHz, CDCl₃): δ 3.22 (t, 2H, J=7.0 Hz), 3.19 (t, 2H, J=7.5 Hz), 5.47 (s, 2H), 7.06 (d, 1H, J=7.5 Hz), 7.30 (t, 2H, J=7.5 Hz), 7.36 (t, 4H, J=8.0 Hz), 7.56 (d, 2H, J=7.5 Hz), 8.02 (d, 1H, J=8.5 Hz); ¹³C-NMR (125 MHz, CDCl₃): δ 35.99, 41.03, 71.29, 111.22, 120.27, 122.22, 125.96, 126.16, 127.21, 127.90, 128.33, 128.59, 128.76, 128.83, 136.37, 137.59, 140.49, 141.98, 154.30, 161.05; HRMS (ESI): 340.17 [M+H]⁺; Yield=47.8%.

Synthesis of Alcohol Protected Quinoline

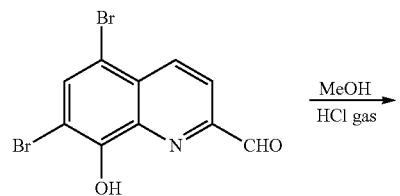

To a stirred solution of 5,7-dibromo-8-hydroxyquinoline-2-carbaldehyde (200 mg, 0.60 mmol) in dry MeOH (20 ml), hydrochloride gas was bubbled at room temperature, after complete reaction the result mixture was stirring for overnight. Then MeOH was removed under reduced pressure to give the designed product 5,7-Dibromo-2-(dimethoxymethyl)quinolin-8-ol (29a) ¹H-NMR (500 MHz, CD₃OD): δ 3.20 (s, 6H), 5.64 (s, 1H), 7.83 (d, 1H, J=8.5 Hz), 7.91 (s, 1H), 8.63 (d, 1H, J=9.0 Hz); ¹³C-NMR (125 MHz, CD₃OD): δ 103.68, 110.12, 112.02, 123.21, 129.38, 137.27, 137.56, 142.59, 151.35, 158.59; HRMS (ESI): Calcd. for C₁₂H₁₂NO₃Br₂ [M+H]⁺, 375.9197. found 375.9184. Yield=88.2%.

Asymmetric Synthesis of 1,2,3,4-Tetrahydroquinoline

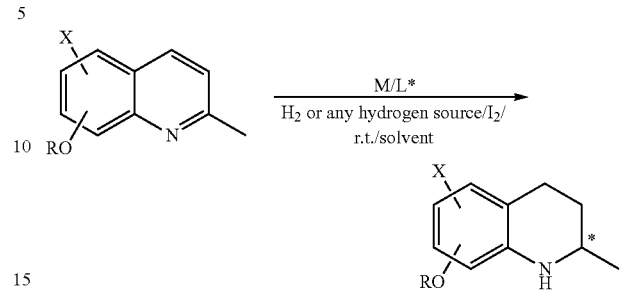

L*=Chiral P-Phos and its derivatives, C₂-symmetric bidendate chiral diphosphines ligands or any other possible ligands; M=Any metal or non-metal complex.

A mixture of metal for example of [Ir(COD)Cl]₂ (1.0 mg, 0.0015 mmol) and the ligand (0.003 mmol) in dried solvent (1.0 mL) was stirred at room temperature for 30 minutes in a glovebox. The mixture was then transferred by a syringe to stainless steel autoclave, in which I₂ (4 mg, 0.015 mmol) and substrate (0.3 mmol) in 0.5 mL dried solvent were placed beforehand. The hydrogenation was performed at room temperature under H₂ for 20 h. After carefully releasing the hydrogen, the reaction mixture was quenched with saturated sodium carbonate solution (2.0 mL) for 15 minutes. The aqueous layer was extracted with EtOAc (3×3 mL). The combined organic layer was dried with sodium sulfate and concentrated in vacuo to give the crude product. Purification by a silica gel column eluted with hexane/EtOAc gave the heterocyclic compound in pure state. The enantiomeric excesses (ee) were determined by chiral HPLC with chiral column (OJ-H, OD-H or OJ) [21].

8-(2-(Piperidin-1-yl)ethoxy)-1,2,3,4-tetrahydro-2-methylquinoline (8b)

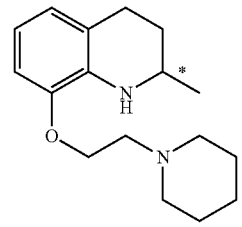 [SMILES: CC1CCc2cccc(OCCN3CCCCC3)c2N1]

¹H-NMR (500 MHz, CDCl₃): δ 0.1 (s, 2H), 1.18 (d, 6H, J=6.5 Hz), 2.11 (s, 4H), 2.53 (bs, 3H), 2.64-2.69 (m, 2H), 2.72-2.81 (m, 3H), 3.30-3.34 (m, 1H), 4.08 (bs, 2H), 6.46 (t, 1H, J=8.0 Hz), 6.56 (t, 2H, J=8.5 Hz); ¹³C-NMR (125 MHz, CDCl₃): δ 22.84, 24.20, 25.82, 26.60, 26.73, 30.26, 46.89, 55.03, 58.05, 66.03, 70.84, 109.38, 115.89, 121.57, 122.11, 135.24, 145.28; LRMS (ESI): 275.21 [M+H]⁺; 47% ee; HPLC(OD-H, elute: Hexanes/i-PrOH=90/10, detector: 254 nm, flow rate: 1.0 mL/min), (S) t₁=8.3 min, (R) t₂=7.1 min.

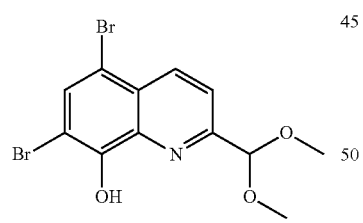

8-(Benzyloxy)-1,2,3,4-tetrahydro-2-methylquinoline (30b)

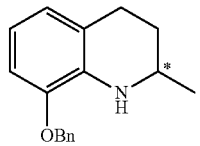 [SMILES: CC1CCc2cccc(OCc3ccccc3)c2N1]

$^{1}$H-NMR (500 MHz, CDCl$_3$): δ 1.25 (d, 3H, J=6.5 Hz), 1.62-1.68 (m, 1H), 1.93-1.98 (m, 1H), 2.75-2.80 (m, 1H), 2.85-2.89 (m, 1H), 3.39-3.43 (m, 1H), 4.21 (bs, 1H), 5.08 (q, 2H, J=6 Hz), 6.56 (t, 1H, J=8.0 Hz), 6.68 (q, 2H, J=8.0 Hz), 7.35 (t, 1H, J=7.0 Hz), 7.42 (t, 2H, J=8.0 Hz), 7.46 (d, 2H, J=7.0 Hz); $^{13}$C-NMR (125 MHz, CDCl$_3$): δ 23.25, 27.04, 30.70, 47.34, 71.04, 109.63, 116.31, 121.96, 122.50, 128.29, 128.57, 129.20, 135.47, 138.06, 145.88; HRMS (ESI): Calcd. for C$_{17}$H$_{20}$NO [M+H]$^{+}$, 254.1545. found 254.1542; [α]$_D^{18}$=+321 (c 0.0048, CHCl$_3$), 93% ee; HPLC (OD-H, elute: Hexanes/i-PrOH=90/10, detector: 254 nm, flow rate: 1.0 ml/min), t$_1$=5.4 min (minor), (R) t$_2$=6.7 min (major).

8-(3-Nitrobenzyloxy)-1,2,3,4-tetrahydro-2-methylquinoline (9b)

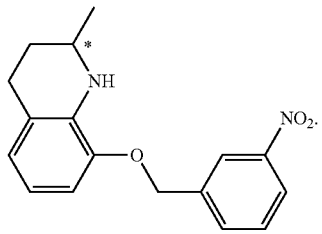 [SMILES: CC1CCc2cccc(OCc3cccc([N+](=O)[O-])c3)c2N1]

$^{1}$H-NMR (500 MHz, CDCl$_3$): δ 1.28 (d, 3H, J=6.5 Hz), 1.61-1.68 (m, 1H), 1.95-2.00 (m, 1H), 2.76-2.81 (m, 1H), 2.85-2.92 (m, 1H), 3.42-3.48 (m, 1H), 4.17 (br, 1H), 5.16 (q, 2H, J=13 Hz), 6.56 (t, 1H, J=7.5 Hz), 6.65 (d, 2H, J=8.0 Hz), 6.70 (d, 1H, J=7.5 Hz), 7.58 (t, 1H, J=8.0 Hz), 7.78 (d, 1H, J=7.5 Hz), 8.20 (d, 1H, J=8.0 Hz), 8.32 (s, 1H); $^{13}$C-NMR (125 MHz, CDCl$_3$): δ 23.18, 26.97, 30.51, 47.31, 69.70, 109.66, 116.28, 122.27, 122.84, 122.99, 123.47, 130.17, 133.92, 135.37, 140.15, 145.15, 148.99; HRMS (ESI): Calcd. for C$_{17}$H$_{19}$N$_2$O$_3$ [M+H]$^{+}$, 299.1396. found 299.1405. [α]$_D^{18}$=+33 (c 0.003, CHCl$_3$), 93% ee; HPLC (AD-H, elute: Hexanes/i-PrOH=99/1, detector: 254 nm, flow rate: 1.0 mL/min), t$_1$=14.0 min (minor), t$_2$=15.5 min (major).

8-(4-Nitrobenzyloxy)-1,2,3,4-tetrahydro-2-methylquinoline (10b)

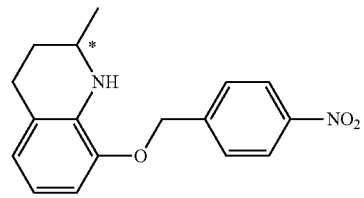 [SMILES: CC1CCc2cccc(OCc3ccc([N+](=O)[O-])cc3)c2N1]

$^{1}$H-NMR (500 MHz, CDCl$_3$): δ 1.29 (d, 3H, J=6.5 Hz), 1.62-1.69 (m, 1H), 1.96-2.01 (m, 1H), 2.76-2.81 (m, 1H), 2.86-2.93 (m, 1H), 3.43-3.47 (m, 1H), 4.16 (br, 1H), 5.18 (q, 2H, J=13 Hz), 6.55 (t, 1H, J=7.5 Hz), 6.61 (d, 2H, J=7.5 Hz), 6.70 (d, 1H, J=7.5 Hz), 7.60 (d, 2H, J=8.5 Hz), 8.24 (d, 2H, J=8.5 Hz); $^{13}$C-NMR (125 MHz, CDCl$_3$): δ 23.18, 26.95, 30.50, 47.32, 69.60, 109.54, 116.30; 122.29, 122.97, 124.37, 128.27, 135.31, 145.08, 145.44, 148.08; HRMS (ESI): Calcd. for C$_{17}$H$_{19}$N$_2$O$_3$ [M+H]$^{+}$, 299.1396. found 299.1405. [α]$_D^{18}$=+76 (c 0.0032, CHCl$_3$), 90% ee; HPLC (AD-H, elute: Hexanes/i-PrOH=90/10, detector: 254 nm, flow rate: 1.0 mL/min), t$_1$=9.5 min (minor), t$_2$=11.6 min (major).

8-(4-Methoxybenzyloxy)-1,2,3,4-tetrahydro-2-methylquinoline (11b)

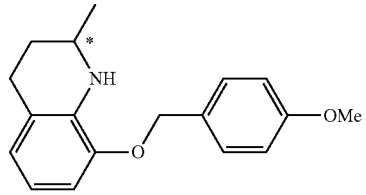 [SMILES: COc1ccc(COc2cccc3c2NC(C)CC3)cc1]

$^{1}$H-NMR (500 MHz, CDCl$_3$): δ 1.28 (d, 3H, J=6.0 Hz), 1.64-1.72 (m, 1H), 1.96-2.01 (m, 1H), 2.79-2.84 (m, 1H), 2.89-2.95 (m, 1H), 3.41-3.46 (m, 1H), 3.87 (s, 1H), 4.23 (br, 1H), 5.03 (q, 2H, J=11 Hz), 6.52 (t, 1H, J=8.0 Hz), 6.71 (d, 1H, J=7.5 Hz), 6.75 (d, 1H, J=8.0 Hz), 6.98 (d, 2H, J=9.0 Hz), 7.42 (d, 2H, J=8.5 Hz); $^{13}$C-NMR (125 MHz, CDCl$_3$): δ 23.18, 26.98, 30.65, 47.25, 55.86, 70.71, 109.54, 114.51, 116.25, 121.80, 122.34, 129.99, 130.01, 135.38, 145.88, 160.02; HRMS (ESI): Calcd. for C$_{18}$H$_{22}$NO$_2$ [M+H]$^{+}$, 284.1651. found 284.1657. [α]$_D^{18}$=+277 (c 0.0033, CHCl$_3$), 92% ee; HPLC (OD-H, elute: Hexanes/i-PrOH=90/10, detector: 254 nm, flow rate: 1.0 mL/min), t$_1$=6.6 min (minor), t$_2$=9.2 min (major).

8-(3-Methoxybenzyloxy)-1,2,3,4-tetrahydro-2-methylquinoline (12b)

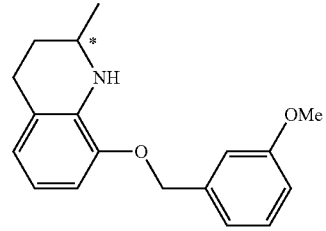 [SMILES: COc1cccc(COc2cccc3c2NC(C)CC3)c1]

$^{1}$H-NMR (500 MHz, CDCl$_3$): δ 1.26 (d, 3H, J=6.5 Hz), 1.61-1.69 (m, 1H), 1.93-1.98 (m, 1H), 2.75-2.80 (m, 1H), 2.85-2.92 (m, 1H), 3.40-3.44 (m, 1H), 3.84 (s, 1H), 4.22 (br, 1H), 5.05 (q, 2H, J=11.5 Hz), 6.56 (t, 1H, J=8.0 Hz), 6.68 (t, 2H, J=8.5 Hz), 6.90 (d, 1H, J=7.5 Hz), 7.03 (t, 2H, J=8.0 Hz), 7.33 (t, 1H, J=8.5 Hz); $^{13}$C-NMR (125 MHz, CDCl$_3$): δ 23.26, 27.03, 30.69, 47.32, 55.90, 70.96, 109.66, 113.71, 114.07, 116.31, 120.47, 121.95, 122.52, 130.24, 135.46, 139.66, 145.83, 160.44; HRMS (ESI): Calcd. for C$_{18}$H$_{22}$NO$_2$, 284.1651. found 284.1657 [M+H]$^{+}$. [α]$_D^{18}$=+543 (c 0.0028, CHCl$_3$), 95% ee; HPLC (OD-H, elute:

Hexanes/i-PrOH=90/10, detector: 254 nm, flow rate: 1.0 mL/min, $t_1$=6.5 min (minor), $t_2$=8.1 min (major).

4-((1,2,3,4-Tetrahydro-2-methylquinolin-8-yloxy)methyl)benzonitrile (13b)

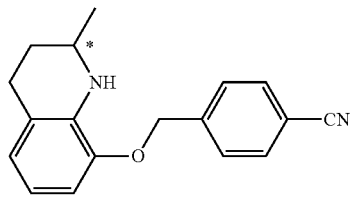 [SMILES: CC1CCc2cccc(OCc3ccc(C#N)cc3)c2N1]

$^1$H-NMR (500 MHz, CDCl$_3$): δ 1.28 (d, 3H, J=6.5 Hz), 1.61-1.69 (m, 1H), 1.96-2.00 (m, 1H), 2.76-2.81 (m, 1H), 2.86-2.92 (m, 1H), 3.42-3.46 (m, 1H), 4.20 (br, 1H), 5.14 (q, 2H, J=13.5 Hz), 6.55 (t, 1H, J=8.0 Hz), 6.61 (d, 2H, J=8.0 Hz), 6.70 (d, 1H, J=7.5 Hz), 7.55 (d, 2H, J=8.0 Hz), 7.68 (d, 2H, J=8.0 Hz); $^{13}$C-NMR (125 MHz, CDCl$_3$): δ 23.16, 26.90, 30.47, 47.25, 69.80, 109.50, 112.15, 116.24, 119.28, 122.17, 122.86, 128.20, 132.92, 135.26, 143.38, 145.09; HRMS (ESI): Calcd. for C$_{18}$H$_{19}$N$_2$O [M+H]$^+$, 279.1497. found 279.1510. [α]$_D^{18}$=+294 (c 0.0012, CHCl$_3$), 93% ee; HPLC (OD-H, elute: Hexanes/i-PrOH=90/10, detector: 254 nm, flow rate: 1.0 mL/min), $t_1$=12.2 min (minor), $t_2$=20.5 min (major).

8-(Biphenyl-3-ylmethoxy)-2-methyl-1,2,3,4-tetrahydroquinoline (14b)

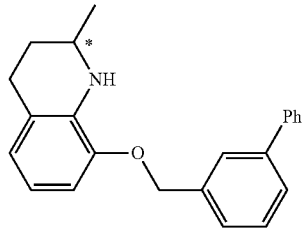 [SMILES: CC1CCc2cccc(OCc3cccc(-c4ccccc4)c3)c2N1]

$^1$H-NMR (500 MHz, CDCl$_3$): δ1.30 (d, 3H, J=6.0 Hz), 1.66-1.74 (m, 1H), 1.98-2.03 (m, 1H), 2.81-2.86 (m, 1H), 2.91-2.98 (m, 1H), 3.44-3.50 (m, 1H), 4.30 (br, 1H), 5.18 (q, 2H, J=11.5 Hz), 6.64 (t, 1H, J=8.0 Hz), 6.74 (d, 1H, J=7.5 Hz), 6.79 (d, 1H, J=8.5 Hz), 7.43 (t, 1H, J=8.0 Hz), 7.48-7.55 (m, 4H), 7.64 (d, 1H, J=7.5 Hz), 7.69 (d, 2H, J=7.0 Hz), 7.75 (s, 1H); $^{13}$C-NMR (125 MHz, CDCl$_3$): δ 23.22, 27.02, 30.66, 47.30, 71.12, 109.74, 116.34, 121.94, 122.56, 127.08, 127.21, 127.36, 127.81, 128.06, 129.43, 129.64, 135.46, 138.56, 141.50, 142.12, 145.87; HRMS (ESI): Calcd. for C$_{23}$H$_{24}$NO [M+H]$^+$, 330.1858. found 330.1874. [α]$_D^{18}$=+131 (c 0.009, CHCl$_3$), 94% ee; HPLC (OD-H, elute: Hexanes/i-PrOH=90/10, detector: 254 nm, flow rate: 1.0 mL/min), $t_1$=7.1 min (minor), $t_2$=8.5 min (major).

8-(4-(Trifluoromethoxy)benzyloxy)-1,2,3,4-tetrahydro-2-methylquinoline (15b)

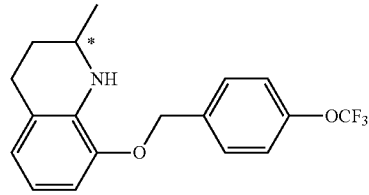 [SMILES: CC1CCc2cccc(OCc3ccc(OC(F)(F)F)cc3)c2N1]

$^1$H-NMR (500 MHz, CDCl$_3$): δ 1.29 (d, 3H, J=6.0 Hz), 1.64-1.72 (m, 1H), 1.97-2.02 (m, 1H), 2.79-2.84 (m, 1H), 2.89-2.95 (m, 1H), 3.42-3.48 (m, 1H), 4.22 (br, 1H), 5.09 (q, 2H, J=12.0 Hz), 6.60 (t, 1H, J=7.5 Hz), 6.71 (t, 2H, J=8.5 Hz), 7.29 (d, 2H, J=7.5 Hz), 7.50 (d, 2H, J=9.0 Hz); $^{13}$C-NMR (125 MHz, CDCl$_3$): δ 23.19, 27.01, 30.62, 47.35, 70.10, 109.61, 116.34, 121.70, 122.12, 122.17, 122.74, 129.60, 135.41, 136.75, 145.57, 149.49; HRMS (ESI): Calcd. for C$_{18}$H$_{19}$NO$_2$F$_3$ [M+H]$^+$, 338.1368. found 338.1367. [α]$_D^{20}$=+30 (c 0.0039, CHCl$_3$), 94% ee; HPLC (OD-H, elute: Hexanes/i-PrOH=90/10, detector: 254 nm, flow rate: 1.0 mL/min), $t_1$=5.0 min (minor), $t_2$=6.8 min (major)

8-(4-Fluorobenzyloxy)-1,2,3,4-tetrahydro-2-methylquinoline (16b)

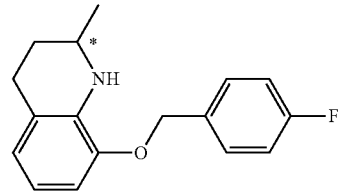 [SMILES: CC1CCc2cccc(OCc3ccc(F)cc3)c2N1]

$^1$H-NMR (500 MHz, CDCl$_3$): δ 1.28 (d, 3H, J=6.0 Hz), 1.63-1.71 (m, 1H), 1.96-2.01 (m, 1H), 2.78-2.84 (m, 1H), 2.88-2.95 (m, 1H), 3.41-3.48 (m, 1H), 4.22 (br, 1H), 5.06 (q, 2H, J=11.5 Hz), 6.60 (t, 1H, J=7.5 Hz), 6.71 (d, 2H, J=8.0 Hz), 7.12 (t, 2H, J=8.5 Hz), 7.45 (t, 2H, J=8.0 Hz); $^{13}$C-NMR (125 MHz, CDCl$_3$): δ 23.19, 26.99, 30.62, 47.31, 70.29, 109.57, 116.13, 122.01, 122.59, 130.06, 130.13, 133.72, 133.75, 135.37, 145.66, 162.13, 164.09; HRMS (ESI): Calcd. for C$_{17}$H$_{19}$NOF [M+H]$^+$, 272.1451. found 272.1458. [α]$_D^{18}$=+74 (c 0.0042, CHCl$_3$), 94% ee; HPLC (OD-H, elute: Hexanes/i-PrOH=90/10, detector: 254 nm, flow rate: 1.0 mL/min), $t_1$=5.4 min (minor), $t_2$=7.1 min (major).

8-(4-(Trifluoromethyl)benzyloxy)-1,2,3,4-tetrahydro-2-methylquinoline (17b)

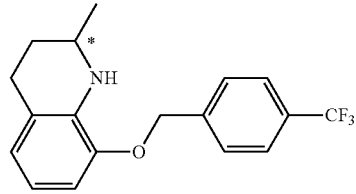 [SMILES: CC1CCc2cccc(OCc3ccc(C(F)(F)F)cc3)c2N1]

¹H-NMR (500 MHz, CDCl₃): δ 1.30 (d, 3H, J=6.0 Hz), 1.64-1.72 (m, 1H), 1.97-2.02 (m, 1H), 2.79-2.84 (m, 1H), 2.88-2.95 (m, 1H), 3.44-3.48 (m, 1H), 4.23 (br, 1H), 5.16 (q, 2H, J=12.5 Hz), 6.59 (t, 1H, J=8.0 Hz), 6.67 (d, 1H, J=8.0 Hz), 6.72 (d, 1H, J=7.5 Hz), 7.58 (d, 2H, J=8.0 Hz), 7.69 (d, 2H, J=8.5 Hz); ¹³C-NMR (125 MHz, CDCl₃): δ 23.22, 27.02, 30.61, 47.37, 70.11, 109.58, 116.35, 122.20, 122.83, 126.16, 128.14, 130.70, 135.39, 142.11, 145.44; HRMS (ESI): Calcd. for $C_{18}H_{19}NOF_3$ [M+H]⁺, 322.1419. found 322.1417. $[α]_D^{18}$=+60 (c 0.002, CHCl₃), 95% ee; HPLC (OD-H, elute: Hexanes/i-PrOH=90/10, detector: 254 nm, flow rate: 1.0 mL/min), $t_1$=5.4 min (minor), $t_2$=7.7 min (major).

8-(4-Chlorobenzyloxy)-1,2,3,4-tetrahydro-2-methylquinoline (18b)

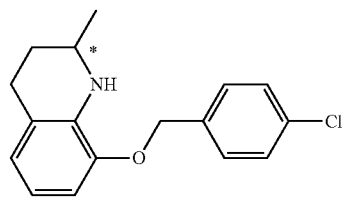 [SMILES: CC1CCc2cccc(OCc3ccc(Cl)cc3)c2N1]

¹H-NMR (500 MHz, CDCl₃): δ 1.27 (d, 3H, J=6.5 Hz), 1.61-1.69 (m, 1H), 1.94-1.99 (m, 1H), 2.76-2.81 (m, 1H), 2.86-2.93 (m, 1H), 3.39-3.46 (m, 1H), 4.18 (br, 1H), 5.04 (q, 2H, J=12.0 Hz), 6.57 (t, 1H, J=7.5 Hz), 6.68 (dd, 2H, J=8.0 Hz), 7.39 (s, 4H); ¹³C-NMR (125 MHz, CDCl₃): δ 23.24, 27.01, 30.63, 47.33, 70.21, 109.58, 116.31, 122.07, 122.66, 129.36, 129.58, 134.34, 135.39, 136.50, 145.57; HRMS (ESI): Calcd. for $C_{17}H_{19}NOCl$ [M+H]⁺, 288.1155. found 288.1161. $[α]_D^{18}$=+254 (c 0.0024, CHCl₃), 95% ee; HPLC (OD-H, elute: Hexanes/i-PrOH=90/10, detector: 254 nm, flow rate: 1.0 mL/min), $t_1$=5.5 min (minor), ($t_2$=7.4 min (major).

8-(Benzyloxy)-1,2,3,4-tetrahydro-2-phenethylquinoline (28b)

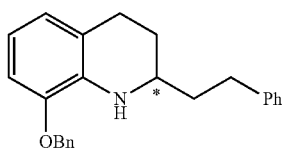 [SMILES: c1ccc(CCC2CCc3cccc(OCc4ccccc4)c3N2)cc1]

¹H-NMR (500 MHz, CDCl₃): δ 1.74-1.78 (m, 1H), 1.79-1.97 (m, 2H), 2.06-2.11 (m, 1H), 2.78-2.94 (m, 4H), 3.33-3.38 (m, 1H), 4.41 (ds, 1H), 5.13 (q, 2H, J=6.0 Hz), 6.62 (t, 1H, J=8.0 Hz), 6.74 (dd, 2H, J=8.0 Hz), 7.23-7.27 (m, 3H), 7.34 (t, 2H, J=7.5 Hz), 7.39 (t, 1H, J=7.0 Hz), 7.46 (t, 2H, J=7.0 Hz), 7.51 (d, 2H, J=7.0 Hz); ¹³C-NMR (125 MHz, CDCl₃): δ 26.59, 28.43, 32.77, 38.79, 51.05, 71.06, 109.80, 116.32, 122.05, 122.48, 126.54, 128.13, 128.54, 129.01, 129.08, 129.20, 135.25, 138.10, 142.52, 145.93; HRMS (ESI): Calcd. for $C_{24}H_{26}NO$ [M+H]⁺, 344.2014. found 344.2029. HPLC (OD-H, elute: Hexanes/i-PrOH=90/10, detector: 254 nm, flow rate: 1.0 mL/min), $t_1$=8.15 min, $t_2$=11.38 min.

2-(3,4-Dimethoxyphenethyl)-1,2,3,4-tetrahydroquinoline (31b)

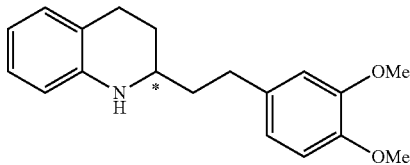 [SMILES: COc1ccc(CCC2CCc3ccccc3N2)cc1OC]

¹H-NMR (500 MHz, CDCl₃): δ 1.67-1.75 (m, 1H), 1.82-1.87 (m, 2H), 2.00-2.05 (m, 1H), 2.71-2.79 (m, 2H), 2.80-2.88 (m, 2H), 3.31-3.36 (m, 1H), 3.90 (d, 6H, J=8.0 Hz), 6.48 (d, 1H, J=7.5 Hz), 6.64 (t, 1H, J=7.5 Hz), 6.78 (d, 2H, J=8.5 Hz), 6.84 (d, 1H, J=8.5 Hz), 6.99 (t, 2H, J=7.0 Hz); ¹³C-NMR (125 MHz, CDCl₃): δ 26.79, 28.59, 32.40, 38.99, 51.79, 56.44, 56.54, 111.97, 112.28, 114.72, 117.59, 120.73, 121.84, 127.31, 129.82, 135.08, 145.11, 147.91, 149.56; HRMS (ESI): Calcd. for $C_{19}H_{24}NO_2$ [M+H]⁺, 298.1807. found 298.1808.

5,7-dibromo-2-methyl-8-(4-(trifluoromethyl)benzyloxy)-1,2,3,4-tetrahydroquinoline (32b)

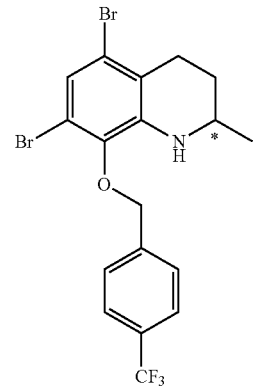 [SMILES: CC1CCc2c(Br)cc(Br)c(OCc3ccc(C(F)(F)F)cc3)c2N1]

¹H-NMR (500 MHz, CDCl₃): δ 1.13 (d, 3H, J=6.0 Hz), 1.46-1.54 (m, 1H), 1.93-1.97 (m, 1H), 2.57-2.64 (m, 1H), 2.78-2.83 (m, 1H), 3.22-3.26 (m, 1H), 4.20 (bs, 1H), 4.98 (q, 2H, J=11 Hz), 7.06 (s, 1H), 7.61 (d, 2H, J=8.0 Hz), 7.67 (d, 2H, J=8.5 Hz); ¹³C-NMR (125 MHz, CDCl₃): δ 22.62, 27.91, 29.94, 46.80, 73.62, 114.77, 121.42, 121.49, 122.64, 126.17, 126.20, 126.23, 126.26, 128.97, 131.07, 141.19, 141.51, 141.55; HRMS (ESI): Calcd. for $C_{18}H_{17}NOF_3Br_2$ [M+H]⁺, 477.9629. found 477.9651. HPLC (OD-H, elute: Hexanes/i-PrOH=90/10, detector: 254 nm, flow rate: 1.0 mL/min, (S) $t_1$=3.99 min, (R) $t_2$=4.89 min.

5,7-dibromo-2-methyl-8-(4-(trifluoromethoxy)benzyloxy)-1,2,3,4-tetrahydroquinoline (33b)

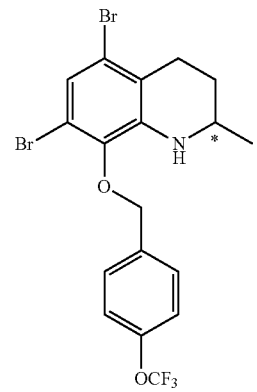 [SMILES: CC1CCc2c(Br)cc(Br)c(OCc3ccc(OC(F)(F)F)cc3)c2N1]

$^1$H-NMR (500 MHz, CDCl$_3$): δ 1.13 (d, 3H, J=6.0 Hz), 1.45-1.53 (m, 1H), 1.92-1.96 (m, 1H), 2.56-2.63 (m, 1H), 2.78-2.83 (m, 1H), 3.19-3.24 (m, 1H), 4.20 (bs, 1H), 4.92 (q, 2H, J=11 Hz), 7.05 (s, 1H), 7.26 (d, 2H, J=8.0 Hz), 7.52 (d, 2H, J=8.5 Hz); $^{13}$C-NMR (125 MHz, CDCl$_3$): δ 22.58, 27.92, 29.95, 46.77, 73.69, 114.80, 120.10, 121.32, 121.39, 121.78, 122.15, 122.58, 130.56, 136.28, 141.19, 141.61, 149.91; HRMS (ESI): Calcd. for C$_{18}$H$_{17}$NO$_2$F$_3$Br$_2$ [M+H]$^+$, 493.9578. found 493.9572. HPLC (OD-H, elute: Hexanes/i-PrOH=90/10, detector: 254 nm, flow rate: 1.0 mL/min), (S) t$_1$=3.83 min, (R) t$_2$=4.54 min.

Synthesis of Quinoline Dimer

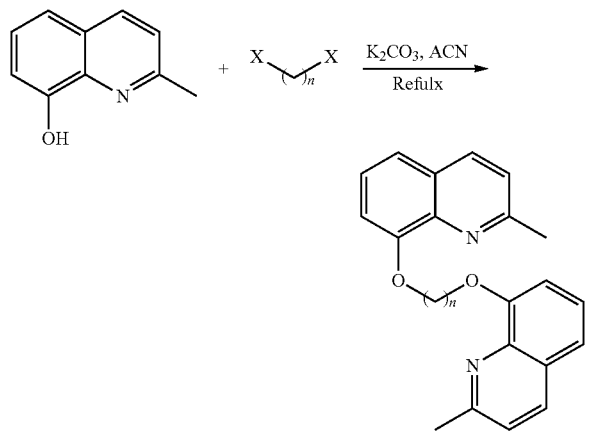

A mixture of 2-methylquinolin-8-ol (2.4 g, 15 mmol) and dihaloalkyl (5 mmol) in ACN was added K$_2$CO$_3$ (2.28 g, 16.5 mmol) and refluxed overnight. Then the ACN was removed and hydrolysed with water. The organic product was extracted with EA (3×50 mL). The combined organic layers were dried over anhydrous sodium sulfate. The solvent was removed under reduced pressure and the crude product was purified by silica gel column chromatography to give the pure product.

1,6-bis(2-methylquinolin-8-yloxy)hexane (34a)

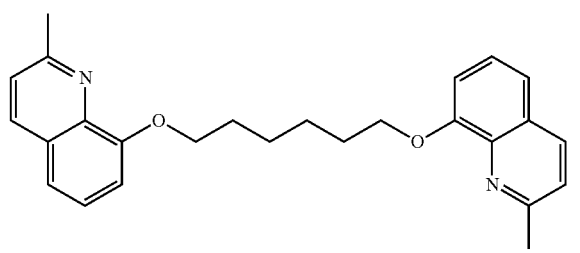 [SMILES: Cc1ccc2cccc(OCCCCCCOc3cccc4ccc(C)nc34)c2n1]

$^1$H-NMR (500 MHz, CDCl$_3$): δ 1.52-1.55 (m, 4H), 1.94-1.97 (m, 4H), 2.64 (s, 6H), 4.13 (t, 4H, J=7.0 Hz), 6.90 (d, 2H, J=7.5 Hz), 7.14 (d, 2H, J=8.5 Hz), 7.18 (d, 2H, J=8.0 Hz), 7.23 (t, 2H, J=8.0 Hz), 7.84 (d, 2H, J=8.5 Hz); $^{13}$C-NMR (100 MHz, CDCl$_3$): δ 26.29, 26.51, 29.44, 69.52, 109.66, 119.88, 122.96, 126.22, 128.26, 136.56, 140.53, 154.89, 158.55; Yield=41.8%.

Synthesis of Soluble Salts of Quinoline Compounds

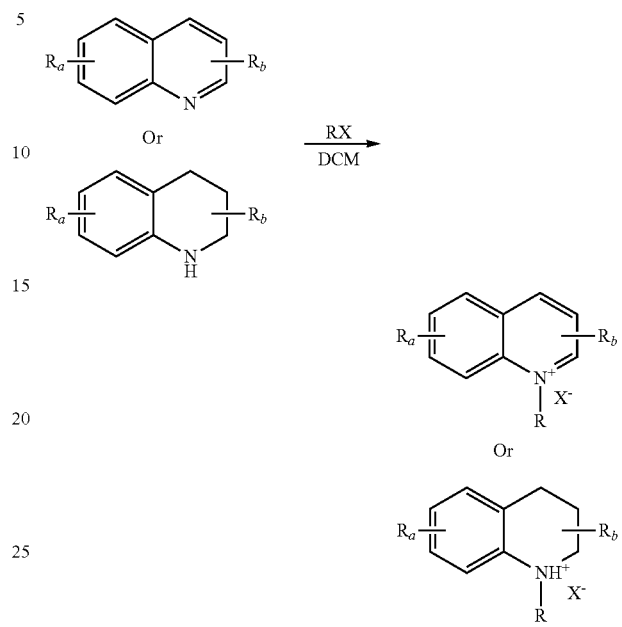

To a stirred solution of quinolines or tetrahydroquinolines (0.57 mmol) in dichloromethane (20 ml), hydrochloride gas was bubbled at room temperature. The precipitate was collected by filtration to give the designed product.

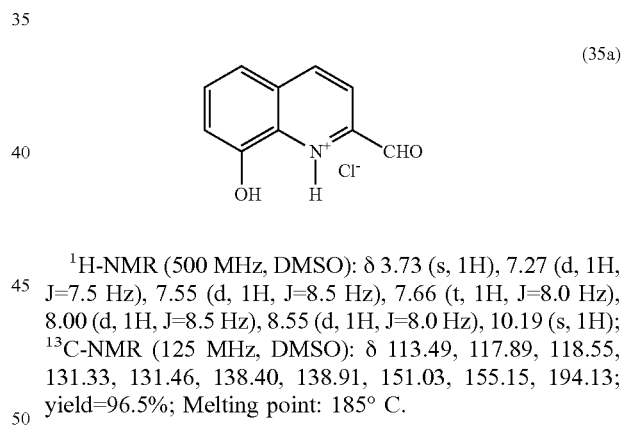
(35a)

$^1$H-NMR (500 MHz, DMSO): δ 3.73 (s, 1H), 7.27 (d, 1H, J=7.5 Hz), 7.55 (d, 1H, J=8.5 Hz), 7.66 (t, 1H, J=8.0 Hz), 8.00 (d, 1H, J=8.5 Hz), 8.55 (d, 1H, J=8.0 Hz), 10.19 (s, 1H); $^{13}$C-NMR (125 MHz, DMSO): δ 113.49, 117.89, 118.55, 131.33, 131.46, 138.40, 138.91, 151.03, 155.15, 194.13; yield=96.5%; Melting point: 185° C.

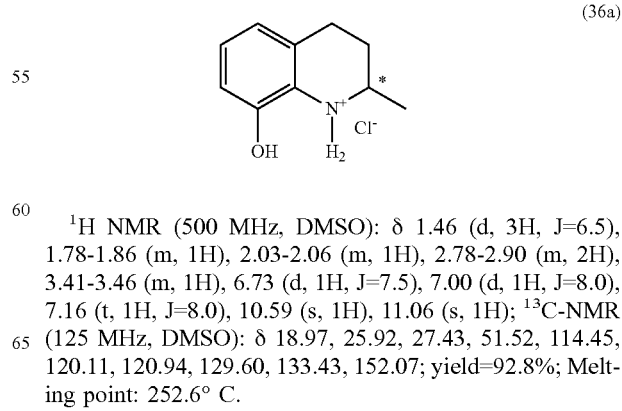
(36a)

$^1$H NMR (500 MHz, DMSO): δ 1.46 (d, 3H, J=6.5), 1.78-1.86 (m, 1H), 2.03-2.06 (m, 1H), 2.78-2.90 (m, 2H), 3.41-3.46 (m, 1H), 6.73 (d, 1H, J=7.5), 7.00 (d, 1H, J=8.0), 7.16 (t, 1H, J=8.0), 10.59 (s, 1H), 11.06 (s, 1H); $^{13}$C-NMR (125 MHz, DMSO): δ 18.97, 25.92, 27.43, 51.52, 114.45, 120.11, 120.94, 129.60, 133.43, 152.07; yield=92.8%; Melting point: 252.6° C.

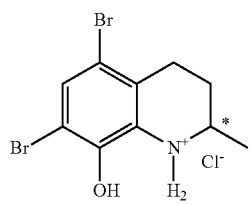

(37a)

$^1$H NMR (500 MHz, DMSO): δ 1.34 (d, 3H, J=5.0), 1.63-1.71 (m, 1H), 1.98-2.03 (m, 1H), 2.59-2.66 (m, 1H), 2.69-2.74 (m, 1H), 3.37-3.41 (m, 1H), 6.42 (bs, 4H), 7.41 (s, 1H); $^{13}$C-NMR (125 MHz, DMSO): δ 20.52, 27.93, 28.30, 49.23, 110.22, 115.93, 126.81, 128.86, 131.33, 145.05.

Lung carcinoma cell line (A549) and hepatocellular carcinoma (HCC) cell line (Hep3B) were obtained from American Type of Culture Collection (ATCC). Esophageal squamous cell carcinoma cell line KYSE150 was purchased from DSMZ (Braunschweig, Germany) [13]. Esophageal squamous cell carcinoma (ESCC) cell line HKESC1 was kindly provided by Professor Gopesh Srivastava of the Department of Pathology, The University of Hong Kong [14]. ESCC cell line HKESC-4 was kindly provided by Professor Simon Law of the Department of Surgery, The University of Hong Kong [15]. Hep3B HCC and A549 lung carcinoma cell lines were maintained in DMEM and F12-K medium respectively with 10% of heat inactivated fetal bovine serum (Hyclone) together with antibiotics involving penicillin and streptomycin. All the ESCC cell lines (KYSE150, HKESC-1 and HKESC-4) were maintained in MEM supplemented with 10% of heat inactivated fetal bovine serum together with antibiotics involving penicillin and streptomycin. Cells were allowed to grow in a humidified cell culture incubator keeping at 5% carbon dioxide.

In Vitro Cytotoxicity Against Cancer Cell Lines

Human liver cancer cell line Hep3B was used for purpose of preliminary anti-cancer screening for the selected alkaloids. Cancer cells (1×10$^4$ per well) seeded in the 96 wells microtitre plates for 24 hours were prepared for the alkaloid screening. The selected compounds were prepared as a stock concentration of 50 mg/ml in dimethylsulfoxide (DMSO) and were added at a concentration of 50 μg/ml and incubated for a further of 48 hours. Untreated control received either total complete medium or 0.1% of DMSO. Cisplatin (CDDP, also at 50 μg/ml) was the positive reference which induced more than 95% in Hep3B. Afterwards, the evaluation of possible antiproliferative or cytotoxicity of those alkaloids was examined by the One Step ATP lite assay purchased from PerkinElmer according to the technical manual provided. Table 1 showed some preliminary results on antitumor activities. The relative MTS activities were compared with the untreated control and illustrated using symbols "+" (more cell death) and "−" (no cytotoxicity).

TABLE 1

Relative anticancer activity among quinoline compounds (50 ug/ml)

Compound Formula B

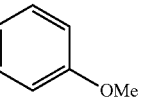

| Compound | R$_1$ | R$_2$ | R$_3$ | R$_4$ | R$_5$ | R$_6$ | R$_7$ | R$_8$ | Relative activity to untreated control |
|---|---|---|---|---|---|---|---|---|---|
| 11a | H | H | H | OH$_2$C–C$_6$H$_4$–OMe (para) | H | CH$_3$ | H | H | +++ |
| 12a | H | H | H | OH$_2$C–C$_6$H$_4$–OMe (meta) | H | CH$_3$ | H | H | +++++ |
| 14a | H | H | H | OH$_2$C–C$_6$H$_4$–Ph (meta) | H | CH$_3$ | H | H | +++++ |
| 15a | H | H | H | OH$_2$C–C$_6$H$_4$–OCF$_3$ (para) | H | CH$_3$ | H | H | +++ |
| 17a | H | H | H | OH$_2$C–C$_6$H$_4$–CF$_3$ (para) | H | CH$_3$ | H | H | +++ |

TABLE 1-continued

| | R1 | R2 | R3 | R4 | R5 | R6 | R7 | R8 | Relative activity to untreated control |
|---|---|---|---|---|---|---|---|---|---|
| 19a | H | H | H | O=S(O₂)CH₂-(camphorsulfonyl) | H | CH₃ | H | H | — |
| 23a | H | H | H | OBn | H | OBn | H | H | +++ |
| 27a | H | H | H | OBn | H | CH₂CH₃ | H | H | +++++ |
| 28a | H | H | H | OBn | H | CH₂CH₂Ph | H | H | ++++ |

Compound Formula A

*Structure: tetrahydroquinoline with R1 at 5-position, R2 at 6, R3 at 7, R4 at 8... R5 on N, R6 at 2, R7 at 3, R8 at 4*

| | R1 | R2 | R3 | R4 | R5 | R6 | R7 | R8 | Relative activity to untreated control |
|---|---|---|---|---|---|---|---|---|---|
| 2b | Br | H | Br | OH | H | CH₃ | H | H | +++++ |
| 5b | H | H | H | OH | H | CH₂OH | H | H | +++++ |
| 8b | H | H | H | O-CH₂CH₂-piperidinyl | H | CH₃ | H | H | + |
| 9b | H | H | H | OH₂C-C₆H₄-(3-NO₂) | H | CH₃ | H | H | — |
| 10b | H | H | H | OH₂C-C₆H₄-(4-NO₂) | H | CH₃ | H | H | — |
| 11b | H | H | H | OH₂C-C₆H₄-(4-OMe) | H | CH₃ | H | H | — |
| 12b | H | H | H | OH₂C-C₆H₄-(3-OMe) | H | CH₃ | H | H | — |
| 13b | H | H | H | OH₂C-C₆H₄-(4-CN) | H | CH₃ | H | H | ++++ |
| 14b | H | H | H | OH₂C-C₆H₄-(3-Ph) | H | CH₃ | H | H | — |
| 15b | H | H | H | OH₂C-C₆H₄-(4-OCF₃) | H | CH₃ | H | H | +++ |

TABLE 1-continued

| | | | | | | | | | |
|---|---|---|---|---|---|---|---|---|---|
| 16b | H | H | H | OH$_2$C-C$_6$H$_4$-F (para) | H | CH$_3$ | H | H | ++ |
| 17b | H | H | H | OH$_2$C-C$_6$H$_4$-CF$_3$ (para) | H | CH$_3$ | H | H | +++++ |
| 18b | H | H | H | OH$_2$C-C$_6$H$_4$-Cl (para) | H | CH$_3$ | H | H | +++ |
| 25b | H | H | H | OAc | H | CH$_3$ | H | H | + |
| 26b | H | H | H | OAc | Ac | CH$_3$ | H | H | + |
| 28a | H | H | H | OBn | H | CH$_2$CH$_2$Ph | H | H | ++++ |
| 24a | 8-OBn, N-Bn quinolin-2(1H)-one | | | | | | | | +++++ |

In Table 1, Formulas A and B are more clearly shown as follows.

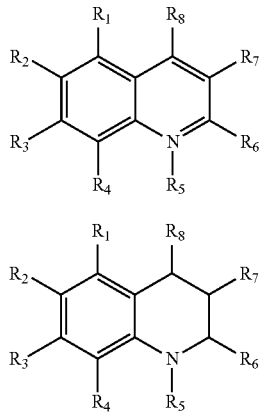

Formula B

Formula A

MTS ([3-(4,5-dimethylthiazol-2-yl)-5-(3-carboxymethoxyphenyl)-2-(4-sulfophen-yl)-H-tetrazolium]) Assay Changes in the cellular viability of compound 11-17a, 9-18b and enantioselective (+)-2b and (−)-2b treated cells were monitored using the MTS activity assay which is known and was reported previously (see reference number 16 below). Results were tabulated in Table 2 and Table 3. Briefly, 1×10$^4$ carcinoma cells were seeded at day 0. After 24 hours, medium was changed and various compounds were added at different concentrations. Cisplatin (CDDP), a commonly used anti-cancer agent, was also used as the positive control. After 48 hours of incubation, the medium was removed and MTS/PMS solution was added and they were incubated further for exactly 30 minutes. Afterwards, optical absorbance was determined at 490 nm according to the user manual (Promega). All the assays were done in triplicates.

TABLE 2

Relative anticancer activity among quinoline compounds

Relative MTS Activity at 50 μg/mL Concentration

| Comp'd | Hep3B | A549 | HKESC-1 | HKESC-4 | HKESC150 |
|---|---|---|---|---|---|
| 11a | 0.320 ± 0.017 | 0.527 ± 0.018 | 0.817 ± 0.076 | 0.488 ± 0.017 | 0.797 ± 0.083 |
| 12a | 0.209 ± 0.030 | n.d. | 0.535 ± 0.032 | 0.794 ± 0.005 | 0.648 ± 0.013 |
| 14a | 0.370 ± 0.214 | 0.244 ± 0.003 | n.d. | n.d. | n.d. |
| 15a | 0.777 ± 0.130 | 0.629 ± 0.081 | n.d. | n.d. | n.d. |
| 17a | 0.878 ± 0.073 | 0.920 ± 0.042 | n.d. | n.d. | n.d. |
| 9b | 0.688 ± 0.027 | 0.706 ± 0.184 | 0.453 ± 0.012 | 0.698 ± 0.096 | 0.619 ± 0.025 |
| 10b | 1.264 ± 0.030 | 1.659 ± 0.173 | 1.337 ± 0.145 | 1.056 ± 0.050 | 1.097 ± 0.036 |
| 11b | 0.554 ± 0.114 | 0.759 ± 0.079 | 0.917 ± 0.023 | 0.777 ± 0.019 | 0.764 ± 0.001 |
| 12b | 0.726 ± 0.065 | n.d. | 0.682 ± 0.001 | 0.716 ± 0.022 | 0.845 ± 0.010 |
| 13b | 0.842 ± 0.024 | n.d. | 0.754 ± 0.017 | 0.424 ± 0.062 | 0.470 ± 0.087 |
| 14b | 0.510 ± 0.068 | 1.238 ± 0.066 | n.d. | n.d. | n.d. |
| 15b | 0.760 ± 0.090 | 0.840 ± 0.029 | n.d. | n.d. | n.d. |

TABLE 2-continued

Relative anticancer activity among quinoline compounds

| | Relative MTS Activity at 50 µg/mL Concentration | | | | |
|---|---|---|---|---|---|
| Comp'd | Hep3B | A549 | HKESC-1 | HKESC-4 | HKESC150 |
| 16b | 0.412 ± 0.017 | 0.908 ± 0.063 | n.d. | n.d. | n.d. |
| 17b | 0.734 ± 0.024 | 0.983 ± 0.001 | n.d. | n.d. | n.d. |
| 18b | 0.609 ± 0.042 | 1.089 ± 0.039 | n.d. | n.d. | n.d. |
| CDDP | 0.116 ± 0.031 | 0.216 ± 0.075 | 0.135 ± 0.017 | 0.158 ± 0.081 | 0.205 ± 0.032 |

In Vitro Studies of (+)-2b and (−)-2b

We screened (+)-2b and (−)-2b for their effects on cell proliferation and potential cytotoxicity in different cell lines. As shown in FIG. 1, both (+)-2b and (−)-2b showed considerable suppressing effects on cancer cell growth with $MTS_{50}$ ranging from 4 to 10 µg/mL.

In the present invention, studies of cytotoxic activity of (+)-2b and (−)-2b (example 11) were carried out on the five carcinoma cell lines (Hep3B, A549, HKESC-1, HKESC-4 and KYSE150) by means of MTS assay. In vitro studies, the (+)-2b showed similar $MTS_{50}$ activity (50% of MTS reduction ability by the chemical treated cell as compared with control) to (−)-2b against the cancer cell lines ($MTS_{50}$=~5 µg/mL). Our preliminary results showed that the (+)-2b exhibited a more than 2-fold cytotoxic activity to the cell line KYSE150 than CDDP, and (+)-2b also exhibited a 1.5-fold cytotoxic activity to the cell lines Hep3B, HKESC-1 and HKESC-4 than CDDP. (+)-2b and (−)-2b showed similar cytotoxic effects on Hep3B, HKESC-4 and A549. These interesting results prompt us to further investigate the underlying molecular mechanisms of antiproliferation.

In Vivo Anti-Cancer Effects of (−)-2b

Optically pure compound (−)-2b (ee up 99%) was tested for their anti-cancer effects against the subcutaneous xenograft tumors of human esophageal cancer derived from the cell line KYSE150, which was purchased from DSMZ (Braunschweig, Germany) and was cultured in a known way as previously described (for details see reference number 17).

Figure 2:
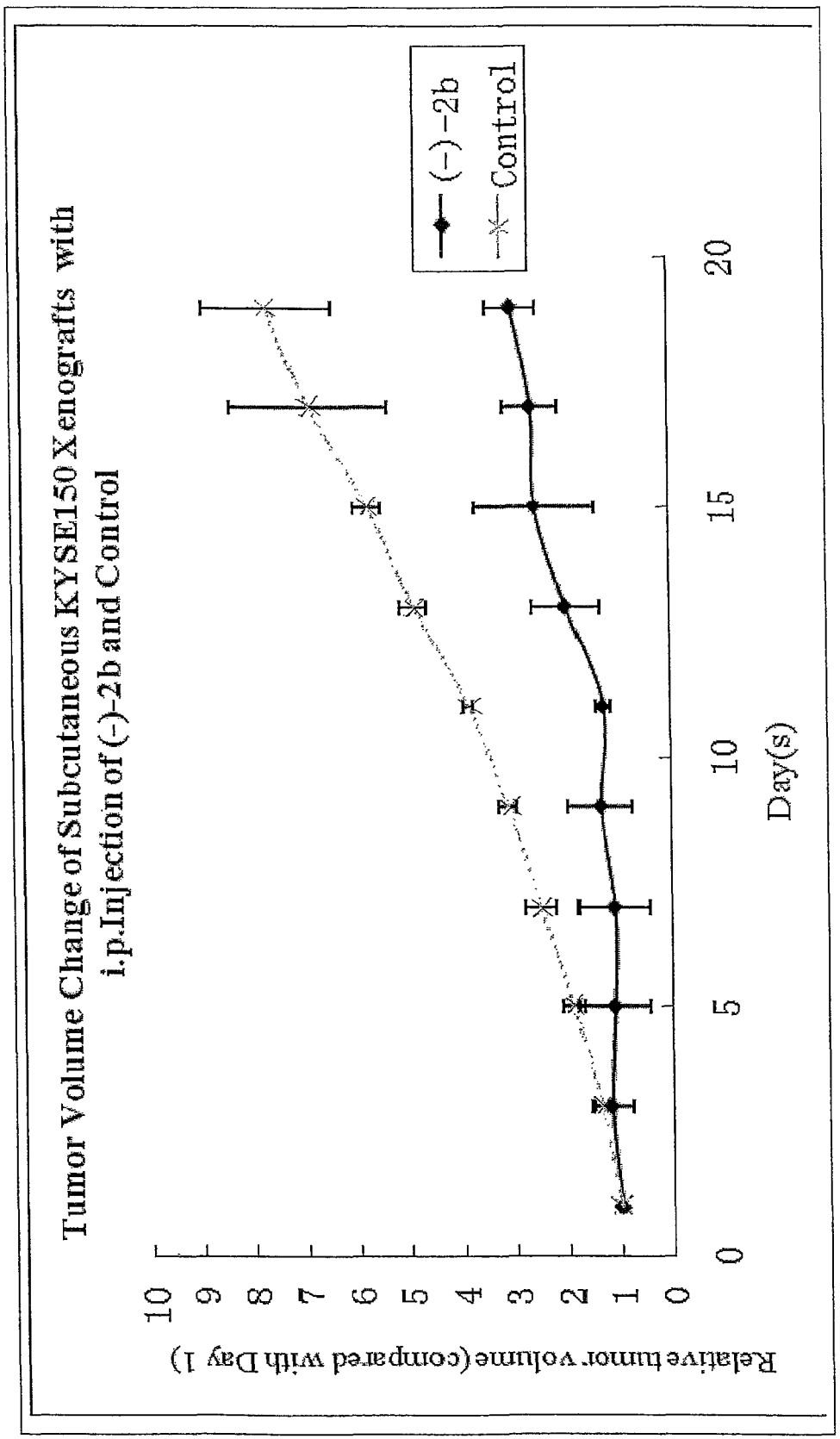
FIG. 2 shows tumor volume change of subcutaneous KYSE150 xenografts with i.p. injection of (−) isomers of 2b and PEG control

Each group of three mice received intra-peritoneal (i.p.) injection daily with 10 mg/kg of optically pure isomers with 6% polyethylene glycol (PEG Mn 8000) for 19 days. The control group of two mice was injected daily with 6% PEG only. Tumor dimensions were measured regularly with calipers, and tumor volumes were estimated using two-dimensional measurements of length and width and calculated with the formula [l×(w)²]×0.52 (l is length and w is width) as previously described. As shown in FIG. 2, the overall results demonstrated that the compound (−)-2b (10 mg/kg/day) is effective in suppressing the volume growth of the KYSE150 xenograft tumors in nude mice compared with the negative control.

Histological examination of liver, heart, lung and kidney sections of the mice after sacrifice showed no observable damage.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

REFERENCES 1. (a) Wang M., Marriott P J., Chan W H., Lee A W M. and Huie C W. *Journal of chromatography A.*, 2006, 1112, 361-368. (c) Betz J M., Gay M L., Mossoba M., Adams S, and Portz B S. *J. AOAC Int.* 1997, 80, 303-315. (d) Karch S B. and Cupp M J. (Eds.) (2000), *Toxicology and Clinical Pharmacology of Herbal Products*, (p. 11) Humana Press, Totowa. (e) Poon C Y. and Chiu P. *Tetrahedron Letters* 2004, 45, 2985-2988. (f) Ojo B., Findsen L A., Igarashi N., Kong B. and Chowdhury B K. *Drug Design and Discovery*, 1996, 14, 1-14.
2. Somberg J C., Ranade V. 'Optically active isomers of quinine and quinidine and their respective biological action.' 2001 (Int. patent no. WO/2001/046188)
3. Zeng H P., Wang T T., Ouyang X H., Zhou Y D., Jing H L., Yuan G Z., Chen D F., Du S H., Li H. and Zhou J H. *Bioorg. & Med. Chem.* 2006, 14, 5446-5450.
4. Musiol R., Jampilek J., Buchta V., Silva L., Niedbala H., Podeszwa B., Palka A., Majerz-Maniecka K., Oleksyn B. and Polanski J. *Bioorganic & Medicinal Chemistry* 2006, 14, 3592-3598.
5. Mandelbaum-Schmid J. *Bull World Health Organ* 2004, 82, 395-396.
6. Sherwood J A., Gachihi G S., Muigai R K., Skillman D R., Mugo M., Rashid J R., Wasunna K M., Were J B., Kasili S K. and Mbugua J M. *Clin Infect Dis* 1994, 19, 1034-1039.
7. Dietze R., Carvalho S F., Valli L C., Berman J., Brewer T., Milhous W., Sanchez J., Schuster B. and Grogl M. *Am J Trop Med. Hyg.* 2001, 65, 685-689.
8. Yeates C. *Curr Opin Investig Drugs* 2002, 3, 1446-1452.
9. Barnham K., Gautier E, Kok G. and Krippner G. 2004, (Int. patent no. WO/2004/007461).
10. Wang W B, Lu S M, Yang P Y, Han X W. and Zhou Y G. *J. Am. Chem. Soc.* 2003, 125, 10536-10537. (b) Lu S M., Han X W. and Zhou Y G. *Adv. Synth. Catal.*, 2004, 346, 909-912. (c) Yang P Y. and Zhou Y G. *Tetrahedron: Asymmetry*, 2004, 15, 1145-1149. (d) Lu S M., Wang Y Q., Han X W. and Zhou Y G. *Angew. Chem. Int. Ed.*, 2006, 45, 2260-2263. (e) Wang X B., Zhou Y G., *Journal of Organic Chemistry* 2008, 73(14), 5640-5642. (f) Xu L J., Lam K H, Ji J X, Wu J, Fan Q H, Lo W H and Chan A S C. *Chem Commun*, 2005, 11, 1390-1392. (g) Lam K H, Xu L J, Feng L C, Fan Q H, Lam F L, Lo W H and Chan A S C. *Adv. Synth. Catal.* 2005, 347, 1755-1758. (h) Tang W J, Zhu S F, Xu L J, Zhou Q L, Fan Q H, Zhou H F, Lam K H and Chan A S C. *Chem Commun*, 2007, 613-615. (i) Chan S H; Lam K H; Li Y M; Xu L J; Tang W J; Lam F L; Lo W H; Yu W Y; Fan Q H; Chan A S C. *Tetrahedron: Asymmetry*, 2007, 18, 2625.

11. (a) Mrsic N, Lefort L, Boogers J A F, Minnaard A J. Feringa B L, de Vries J G. *Adv. Synth. Catal.* 2008, 350(7), 1081-1089. (b) Deport C, Buchotte M, Abecassis K, Tadaoka H, Ayad T, Ohshima T, Genet J P, Mashima K, Ratovelomanana-Vidal V. *Synlett.* 2007, 17, 2743-2747. (c) Reetz M T, Li X G. *Chem. Comm.* 2006, 20, 2159-2160.
12. Chan, A S C.; Tang, J C O.; Lam, K H.; Chui, C H.; Kok, S H L.; Chan, S H; Cheung, F; Gambari, R.; Cheng, C H 'Method of Making and Administering Quinoline Derivatives as Anti-Cancer Agents.' 2009 (Int. patent no. WO2009024095A1)
13. Shimada Y., Imamura M., Wagata T., Yamaguchi N. and Tobe T. *Cancer* 1992, 69, 277-284.
14. Hu Y C., Lam K Y., Wan T S., Fang W., Ma E S., Chan L C., Srivastava G. *Cancer Genet Cytogenet* 2000, 118, 112-20.
15. Cheung L C M., Tang J C O., Lee P Y., Hu L., Guan X Y., Tang W K., Srivastava G, Wong J., Luk J., Law S. *Cancer Genetics and Cytogenetics* 2007, 178 (1), 17-25.
16. (a) Chui, C H.; Cheng, G Y.; Ke, B.; Lau, F Y.; Wong, R S.; Kok, S H.; Fatima, S.; Cheung, F.; Cheng, C H.; Chan, A S C. Tang, J C O. *Int. J. Mol. Med.* 2004, 14, 975-979; (b) Kok, S H L.; Chui, H C.; Lam, W S.; Chen, J.; Lau, F Y.; Wong, R S. M.; Cheng, G Y M.; Tang, W K.; Cheng, C H.; Tang, J C O.; Chan, A S C. *Int. J. Mol. Med.* 2006, 18, 375-379; (c) Kok, S H L.; Gambari, R.; Chui, H C.; Lam, W S.; Chen, J.; Lau, F Y.; Wong, R S M.; Cheng, G Y M.; Lai, P B S.; Leung, T W T.; Chan, A S C.; Tang, J C O. *Minerva Biotecnologica,* 2006, 18, 153-157; (d) Kok, S H L.; Chui, H C.; Lam, W S.; Chen, J.; Lau, F Y.; Wong, R S M.; Cheng, G Y M.; Tang, W K.; Teo, I T N.; Cheung, F.; Cheng, C H.; Chan, A S C.; Tang, J C O. *Int. J. Mol. Med.* 2006, 18, 1217-1221; (e) Kok, S H L.; Chui, H C.; Lam, W S.; Chen, J.; Lau, F Y.; Wong, R S M.; Cheng, G Y M.; Lai, P B S.; Leung, T W T.; Tang, J C O.; Chan, A S C. *Bioorg. Med. Chem. Lett.* 2007, 17, 1155-1159.
17. Shimada Y., Imamura M., Wagata T., Yamaguchi N. and Tobe T. *Cancer* 1992, 69, 277-284.
18. Guba M., von Breitenbuch P., Steinbauer M., Koehl G., Flegel S., Hornung M., Bruns C J., Zuelke C., Farkas S., Anthuber M., Jauch K W., Geissler E K. *Nature Medicine* 2002, 8, 128-35.

What is claimed is:

1. A quinoline derivative, comprising a structure of the following formula:

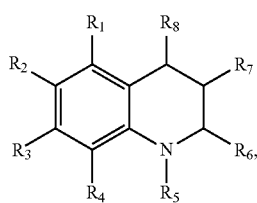

wherein $R_1$ and $R_3$ are independently of each other H or Br;
wherein each of $R_2$, $R_7$ and $R_8$ is H;
wherein $R_4$ is CN, 2-(piperdin-1-yl)ethoxy, biphenyl-3-ylmethoxy, OH, OAc, or OR', wherein R' is a phenyl group having the following formula:

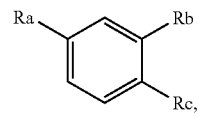

wherein $R_a$ is $CH_2$ or $SO_2$; $R_b$ and $R_c$ independently are H, Cl, F, $OCH_3$, $CH_3$, Ph, $NO_2$, $CF_3$ or $OCF_3$;
wherein $R_5$ is H or $COCH_3$;
wherein $R_6$ is $CH_3$, OH, $CH_2OH$, $CH_2CH_2Ph$, $CH_2CH_3$, OBn, COOH, CHO, 3,4-dimethoxyphenethyl or a phenyl group having the following formula:

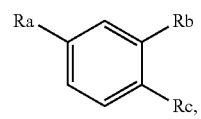

wherein $R_a$ is $CH_2NH$; $R_b$ and $R_c$ independently of each other are H, $C(CH_3)_3$, $OCH_3$, OPh, $COH_2Ph$ or morpholinyl;
provided that when $R_2$, $R_5$, $R_7$ and $R_8$ are H, and $R_4$ is OH, then $R_6$ is not $CH_3$;
provided that when $R_1$, $R_2$, $R_3$, $R_7$ and $R_8$ are H, $R_6$ is $CH_3$, and $R_4$ is an alkoxy, then $R_5$ is not H; and
provided that when $R_1$ is Br, $R_2$, $R_3$, $R_5$, $R_7$ and $R_8$ are H, and $R_6$ is $CH_3$, then $R_4$ is not OH;
and salts thereof.

2. The quinoline derivative of claim 1, wherein $R_6$ is selected from the group consisting of $CH_3$, $CH_2OH$, $CH_2CH_2Ph$, and OH; and wherein $R_4$ is OH, OAc or OR' wherein R' is a phenyl group having the following formula:

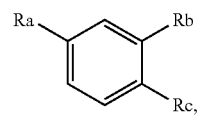

wherein $R_a$ is $CH_2$ or $SO_2$, $R_b$ and $R_c$ independently are H, Cl, F, $OCH_3$, $CH_3$, Ph, $NO_2$, $CF_3$ or $OCF_3$.

3. The quinoline derivative of claim 1, wherein $R_6$ is selected from the group consisting of $CH_2CH_3$, OBn, COOH and CHO; and $R_4$ is OH, OAc or OR' wherein R' is a phenyl group having the following formula:

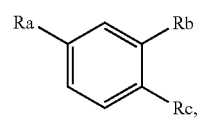

wherein $R_a$ is $CH_2$ or $SO_2$, $R_b$ and $R_c$ independently are H, Cl, F, $OCH_3$, $CH_3$, Ph, $NO_2$, $CF_3$ or $OCF_3$.

4. The quinoline derivative of claim 2, wherein $R_6$ is $CH_3$.

5. The quinoline derivative of claim 2, wherein $R_4$ is OH; and wherein $R_6$ is OH.

6. The quinoline derivative of claim 3, wherein $R_4$ is OAc; and wherein $R_6$ is COOH.

7. The quinoline derivative of claim 1, wherein $R_1$ and $R_3$ are H; wherein $R_6$ is $CH_3$; and wherein $R_4$ is OR' wherein R' is a phenyl group of the following formula:

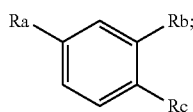

and
wherein Ra is CH$_2$, Rb is H, OCH$_3$, NO$_2$ or Ph, and Rc is H, Ph, F, Cl, OCF$_3$, CF$_3$, CN, OCH$_3$ or NO$_2$.

8. The quinoline derivative of claim 7, wherein Rb is H and Rc is OCH$_3$, NO$_2$, F, Cl, CF$_3$ or OCF$_3$.

9. A quinoline derivative having a structure of the following formula:

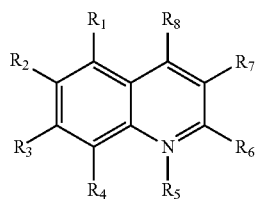

wherein R$_2$, R$_5$, R$_7$, and R$_8$ are H;
wherein R$_1$ and R$_3$ are Br;
wherein R$_6$ is CH$_3$; and
wherein R$_4$ is OAc or OH; and
wherein, when R$_4$ is OH and when the quinoline derivative comprises the following formula:

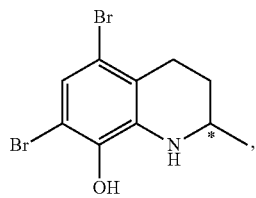

* represents a chiral center of the quinoline derivative; and salts thereof.

10. A method of treating cancer in a mammal, the method comprising the step of administering to the mammal a quinoline derivative of claim 1 in an amount from about 8 to about 12 mg/kg/day body weight with a pharmaceutically acceptable carrier.

11. The method of claim 10, wherein said quinoline derivative is administered over a continuous period of between 5 to 10 days.

12. The method of claim 10, wherein said cancer is breast carcinoma, hepatocellulor carcinoma, or chronic myelogenous leukemia.

13. The method of claim 10, wherein said quinoline derivative is a chiral or non-chiral tetrahydroquinoline derivative.

14. A quinoline derivative, wherein said quinoline derivative is a substituted quinoline selected from the group consisting of 5,7-dibromo-1,2,3,4-tetrahydro-2-methylquinolin-8-ol and 1,2,3,4-tetrahydro-2-(hydroxymethyl)quinolin-8-ol.

15. The quinoline derivative of claim 1, wherein said quinoline derivative is selected from the group consisting of 2-methyl-1,2,3,4-tetrahydroquinolin-8-yl acetate, and 1-acetyl-2-methyl-1,2,3,4-tetrahydroquinoline-8-yl acetate.

16. The quinoline derivative of claim 1, wherein said quinoline derivative is selected from the group consisting of 8-(2-(piperidin-1-yl)ethoxy)-1,2,3,4-tetrahydro-2-methylquinoline, 8-(benzyloxy)-1,2,3,4-tetrahydro-2-methylquinoline, 8-(3-nitrobenzyloxy)-1,2,3,4-tetrahydro-2-methylquinoline, 8-(4-nitrobenzyloxy)-1,2,3,4-tetrahydro-2-methylquinoline, 8-(4-methoxybenzyloxy)-1,2,3,4-tetrahydro-2-methylquinoline, 8-(3-methoxybenzyloxy)-1,2,3,4-tetrahydro-2-methylquinoline, 4-((1,2,3,4-tetrahydro-2-methylquinolin-8-yloxy)methyl)benzonitrile, 8-(biphenyl-3-ylmethoxy)-2-methyl-1,2,3,4-tetrahydroquinoline, 8-(4-(trifluoromethoxy)benzyloxy)-1,2,3,4-tetrahydro-2-methylquinoline, 8-(4-fluorobenzyloxy)-1,2,3,4-tetrahydro-2-methylquinoline, 8-(4-(trifluoromethyl)benzyloxy)-1,2,3,4-tetrahydro-2-methylquinoline, 8-(4-chlorobenzyloxy)-1,2,3,4-tetrahydro-2-methylquinoline, 8-(benzyloxy)-1,2,3,4-tetrahydro-2-phenethylquinoline, 2-(3,4-dimethoxyphenethyl)-1,2,3,4-tetrahydroquinoline, 5,7-dibromo-2-methyl-8-(4-(trifluoromethyl)benzyloxy)-1,2,3,4-tetrahydroquinoline, and 5,7-dibromo-2-methyl-8-(4-(trifluoromethoxy)benzyloxy)-1,2,3,4-tetrahydroquinoline.

17. The quinoline derivative of claim 1,
wherein R$_1$ and R$_3$ are H;
wherein R$_6$ is CH$_3$; and
wherein R$_4$ is 4-(trifluoromethyl)benzyloxy.

18. The quinoline derivative of claim 1, wherein R$_4$ is OR' wherein R' is a phenyl group of the following formula:

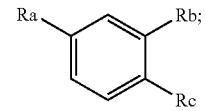

and
wherein Ra is CH$_2$, Rb is H, OCH$_3$, NO$_2$ or Ph, and Rc is H, Ph, F, Cl, OCF$_3$, CF$_3$, CN, OCH$_3$ or NO$_2$.

19. A method of treating cancer in a mammal, the method comprising the step of administering to the mammal a pharmaceutical composition comprising
(i) the quinoline derivative of claim 14; and
(ii) a pharmaceutically acceptable carrier.

20. The method according to claim 19, wherein the step of administering comprises administering the quinoline derivative in an amount from about 8 to about 12 mg per kg body weight of the mammal.

21. The method according to claim 19, wherein the quinoline derivative is administered to the mammal daily over a continuous period of between 5 to 10 days.

22. The method according to claim 19, wherein the cancer is breast carcinoma, hepatocellulor carcinoma, or chronic myelogenous leukemia.

* * * * *